US008854628B2

(12) United States Patent
Colonna de Lega et al.

(10) Patent No.: US 8,854,628 B2
(45) Date of Patent: Oct. 7, 2014

(54) INTERFEROMETRIC METHODS FOR METROLOGY OF SURFACES, FILMS AND UNDERRESOLVED STRUCTURES

(75) Inventors: Xavier M. Colonna de Lega, Middlefield, CT (US); Peter J. de Groot, Middletown, CT (US); Jan Liesener, Middletown, CT (US)

(73) Assignee: Zygo Corporation, Middlefield, CT (US)

( * ) Notice: Subject to any disclaimer, the term of this patent is extended or adjusted under 35 U.S.C. 154(b) by 332 days.

(21) Appl. No.: 13/238,732

(22) Filed: Sep. 21, 2011

(65) Prior Publication Data

US 2012/0069326 A1 Mar. 22, 2012

Related U.S. Application Data

(60) Provisional application No. 61/385,397, filed on Sep. 22, 2010.

(51) Int. Cl.
| | |
|---|---|
| G01B 9/02 | (2006.01) |
| G01B 11/02 | (2006.01) |
| G01N 21/41 | (2006.01) |
| G01N 21/43 | (2006.01) |
| G01N 21/21 | (2006.01) |
| G01N 21/45 | (2006.01) |
| G01N 21/47 | (2006.01) |
| G01B 11/06 | (2006.01) |

(52) U.S. Cl.
CPC ............ *G01B 9/02043* (2013.01); *G01N 21/21* (2013.01); *G01N 21/45* (2013.01); *G01N 21/47* (2013.01); *G01B 2290/70* (2013.01); *G01B 9/02057* (2013.01); *G01B 9/0209* (2013.01); *G01B 11/0675* (2013.01)

USPC ........... 356/491; 356/481; 356/495; 356/504; 356/517

(58) Field of Classification Search
None
See application file for complete search history.

(56) References Cited

U.S. PATENT DOCUMENTS

| | | | |
|---|---|---|---|
| 5,450,205 A * | 9/1995 | Sawin et al. ................. | 356/632 |
| 7,061,623 B2 | 6/2006 | Davidson | |
| 7,095,507 B1 * | 8/2006 | Hwang et al. ................ | 356/512 |
| 7,428,057 B2 | 9/2008 | Colonna de Lega | |
| 7,446,882 B2 | 11/2008 | Colonna de Lega | |
| 2003/0030819 A1 * | 2/2003 | Kuechel ....................... | 356/512 |
| 2004/0130726 A1 * | 7/2004 | Mikkelsen et al. .......... | 356/504 |
| 2005/0068540 A1 * | 3/2005 | De Groot et al. ............ | 356/512 |
| 2006/0158659 A1 * | 7/2006 | Colonna De Lega et al. ............................. | 356/497 |
| 2006/0175528 A1 * | 8/2006 | Greenaway et al. ........ | 250/201.9 |
| 2009/0021723 A1 * | 1/2009 | De Lega ....................... | 356/73 |
| 2009/0182528 A1 * | 7/2009 | De Groot et al. ............ | 702/167 |

* cited by examiner

*Primary Examiner* — Tarifur Chowdhury
*Assistant Examiner* — Hina F Ayub
(74) *Attorney, Agent, or Firm* — Fish & Richardson P.C.

(57) ABSTRACT

A method for determining information about a test object includes combining two or more scanning interference signals to form a synthetic interference signal; analyzing the synthetic interference signal to determine information about the test object; and outputting the information about the test object. Each of the two or more scanning interference signals correspond to interference between test light and reference light as an optical path length difference between the test and reference light is scanned, wherein the test and reference light are derived from a common source. The test light scatters from the test object over a range of angles and each of the two or more scanning interferometry signals corresponds to a different scattering angle or polarization state of the test light.

42 Claims, 11 Drawing Sheets

INTERFEROMETRIC METHODS FOR METROLOGY OF SURFACES, FILMS AND UNDERRESOLVED STRUCTURES

BACKGROUND

The invention relates to optical metrology of surfaces, films, and unresolved structures.

Interferometric techniques are commonly used to measure the profile of a surface of an object. To do so, an interferometer combines a measurement wavefront reflected from the surface of interest with a reference wavefront reflected from a reference surface to produce an interferogram. Fringes in the interferogram are indicative of spatial variations between the surface of interest and the reference surface.

A scanning interferometer scans the optical path length difference (OPD) between the reference and measurement legs of the interferometer over a range comparable to, or larger than, the coherence length of the interfering wavefronts, to produce a scanning interference signal for each camera pixel used to measure the interferogram. A limited coherence length can be produced, for example, by using a white-light source, which is referred to as scanning white light interferometry (SWLI). A typical scanning white light interferometry (SWLI) signal is a few fringes localized near the zero optical path difference (OPD) position. The signal is typically characterized by a sinusoidal carrier modulation (the "fringes") with bell-shaped fringe-contrast envelope. The conventional idea underlying SWLI metrology is to make use of the localization of the fringes to measure surface profiles.

SWLI processing techniques include two principal trends. The first approach is to locate the peak or center of the envelope, assuming that this position corresponds to the zero optical path difference (OPD) of a two-beam interferometer for which one beam reflects from the object surface. The second approach is to transform the signal into the frequency domain and calculate the rate of change of phase with wavelength, assuming that an essentially linear slope is directly proportional to object position. See, for example, U.S. Pat. No. 5,398,113 to Peter de Groot. This latter approach is referred to as Frequency Domain Analysis (FDA).

Scanning interferometry can be used to measure surface topography and/or other characteristics of objects having complex surface structures, such as thin film(s), discrete structures of dissimilar materials, or discrete structures that are underresolved by the optical resolution of an interference microscope. By "underresolved" it is meant that the individual features of the object are not fully separated in a surface profile image taken using the interference microscope as a consequence of the limited lateral resolution of the instrument. Surface topography measurements are relevant to the characterization of flat panel display components, semiconductor wafer metrology, and in-situ thin film and dissimilar materials analysis. See, e.g., U.S. Patent Publication No. US-2004-0189999-A1 by Peter de Groot et al. entitled "Profiling Complex Surface Structures Using Scanning Interferometry" and published on Sep. 30, 2004, the contents of which are incorporated herein by reference, and U.S. Patent Publication No. US-2004-0085544-A1 by Peter de Groot entitled "Interferometry Method for Ellipsometry, Reflectometry, and Scatterometry Measurements, Including Characterization of Thin Film Structures" and published on May 6, 2004, the contents of which are incorporated herein by reference.

Other techniques for optically determining information about an object include ellipsometry and reflectometry. Ellipsometry determines complex reflectivity of a surface when illuminated at an oblique angle, e.g., 60°, sometimes with a variable angle or with multiple wavelengths. To achieve greater resolution than is readily achievable in a conventional ellipsometer, microellipsometers measure phase and/or intensity distributions in the back focal plane of the objective, also known as the pupil plane, where the various illumination angles are mapped into field positions. Such devices are modernizations of traditional polarization microscopes or "conoscopes," linked historically to crystallography and mineralogy, which employs crossed polarizers and a Bertrand lens to analyze the pupil plane in the presence of birefringent materials.

Conventional techniques used for thin film characterization (e.g., ellipsometry and reflectometry) rely on the fact that the complex reflectivity of an unknown optical interface depends both on its intrinsic characteristics (material properties and thickness of individual layers) and on three properties of the light that is used for measuring the reflectivity: wavelength, angle of incidence, and polarization state. In practice, characterization instruments record reflectivity fluctuations resulting from varying these parameters over known ranges. Optimization procedures such as least-squares fits are then used to get estimates for the unknown parameters by minimizing the difference between measured reflectivity data and a reflectivity function derived from a model of the optical structure.

Interferometers having multiple modes for determining characteristics of an object are disclosed in US 2006-0158657 A1 (now U.S. Pat. No. 7,428,057) and US 2006-0158658 A1, the entire contents both of which are incorporated herein by reference.

SUMMARY

Synthetic interference signals can be generated from scanning interference signals recorded at multiple pupil positions (e.g., corresponding to different polar angles of incidence but along a constant azimuth) in order to reduce (e.g., eliminate) or enhance the signal content corresponding to specific features of the object surface (such as material interfaces or scattering structures). This preliminary signal processing can simplify the process of matching experimental to model data. For instance, in the case of a patterned structure of interest that covers another buried patterned structure, eliminating from the synthetic interference signal the information related to the buried structure similarly eliminates the need to model light interaction with the buried structure. The resulting model may be simpler, providing for faster and more robust analysis (e.g., using fewer model parameters).

Various aspects of the invention are summarized as follows.

In general, in one aspect, the invention features a method for determining information about a test object, the method including combining two or more scanning interference signals to form a synthetic interference signal; analyzing the synthetic interference signal to determine information about the test object; and outputting the information about the test object. Each of the two or more scanning interference signals correspond to interference between test light and reference light as an optical path length difference between the test and reference light is scanned, wherein the test and reference light are derived from a common source. The test light scatters from the test object over a range of angles and each of the two or more scanning interferometry signals corresponds to a different scattering angle or polarization state of the test light.

Implementations of the method can include one or more of the following features. For example, a contribution to the two or more scanning interference signals from a structure of the test object can be suppressed or enhanced in the synthetic interference signal relative to the two or more scanning interference signals.

In some embodiments, the structure is an interface between two different materials from which the test object is composed. A contribution from the interface to the two or more scanning interference signals can be reduced in the synthetic interference signal.

The structure can be a first patterned structure of the test object. The information about the test object can be information about a second patterned structure of the test object different from the first patterned structure. The first and second patterned structured can be in different layers of the test object. The first patterned structure can be a buried structure. A contribution from the first patterned structure to the two or more scanning interference signals can be reduced in the synthetic interference signal.

Determining information about the test object can include comparing the synthetic interference signal or information derived from the synthetic interference signal to model data, where the model data does not include a contribution from the first patterned structure.

The first patterned structure can include one or more holes in a layer of the test object. The first patterned structure can include one or more lines of a grating of the test object. The first patterned structure can include one or more mesas in the test object.

The test object can include a layer of a semiconductor material. The test object can include a layer of a photoresist material (e.g., a patterned layer of photoresist).

Combining the two or more scanning interference signals can include combining values for the two or more scanning interference signals for each of multiple scan positions of the optical path length difference. Combining the values can include summing the values. Summing the values can include taking a weighted sum of the values. The values can be weighted according to a predetermined weighting function. The weights for the weighted sum can be determined based on a smoothly varying function. In some embodiments, contributions to the synthetic interference signal from scanning interference signals corresponding to higher polar scattering angles are weighted more heavily that contributions corresponding to scanning interference signals from lower polar scattering angles. Summing the values can include averaging the values.

Combining the two or more scanning interference signals can include weighting contributions from the two or more scanning interference signals to the synthetic interference signal so that a contribution to the synthetic interference signal from a structure of the test object is suppressed relative to a contribution from the structure to the two or more scanning interference signals.

Combining the two or more scanning interference signals can include weighting contributions from the two or more scanning interference signals to the synthetic interference signal so that a contribution to the synthetic interference signal from a buried structure of the test object is enhanced relative to a contribution to the two or more scanning interference signals from the buried structure.

The two or more scanning interference signals can correspond to different polar scattering angles of the test light from the test object. The two or more scanning interference signals can correspond to the same azimuthal scattering angle.

Determining information about the test object can include comparing the synthetic interference signal or information derived from the synthetic interference signal to model data. Comparing the synthetic interference signal to model data can include matching the synthetic interference signal to a model signal in a library of model signals. Comparing the synthetic interference signal to the model data can include performing a regression of parameters of a model of the test object structure.

The test object can include a first layer of a material and the information about the test object is a refractive index of the material. A contribution from an interface between the first layer and an adjacent layer to the two or more scanning interference signals can be reduced in the synthetic interference signal. Determining information about the test object can include comparing the synthetic interference signal or information derived from the synthetic interference signal to model data, where the model data is determined based on a model that does not depend on a thickness of the first layer.

The synthetic interference signal can include contributions from a plurality of frequency components and analysis of the synthetic interference signal is performed for only a subset of frequency components of the synthetic interference signal. Analysis of the synthetic interference signal can include determining a frequency transform of the synthetic interference signal. The frequency transform can be a Fourier transform.

Determining information about the test object can include comparing information derived from the synthetic interference signal to model data, where the model data is determined for a subset of wavelengths present in light used to generate the two or more scanning interference signals.

The method can include generating one or more additional synthetic interference signals from the one or more of the scanning interference signals. Each of the synthetic interference signals can correspond to different illumination conditions of the test object. The different illumination conditions can correspond to different polarization states of the test light.

In general, in another aspect, the invention features a method for determining information about a test object, including simultaneously acquiring two or more scanning interference signals, wherein each of the two or more scanning interference signals correspond to interference between test light and reference light as an optical path length difference between the test and reference light is scanned, wherein the test and reference light are derived from a common source, and wherein the test light scatters from the test object over a range of angles and each of the two or more scanning interferometry systems corresponds to a different scattering angle or polarization state of the test light; combining values of the two or more scanning interference signals for each scan position of the optical path difference to form a combined signal in which a contribution to the combined signal from a feature of the test object is reduced relative to the contribution of the feature to the two or more scanning interferometry signals; analyzing the combined signal to determine information about the test object; and outputting the information about the test object, Implementations of the method can include one or more of the features of other aspects.

In general, in a further aspect, the invention features an apparatus that includes an interferometer configured to direct test light to a test surface over a range of illumination angles and subsequently combine it with reference light to form an interference pattern, the test and reference light being derived from a common source; the common source; a multi-element detector; one or more optics configured to direct at least a portion of the combined light to the detector so that different elements of the detector correspond to different illumination angles of the test surface by the test light; and an electronic processing system coupled to the multi-element detector, which during operation receives two or more scanning interference signals from the multi-element detector, combines the two or more scanning interference signals to form a synthetic interference signal and analyzes the synthetic interference signal to determine information about the test object.

Embodiments of the apparatus can include one or more features of the other aspects.

A variety of different test objects can be studied using the disclosed techniques. For example, test objects featuring complex surface structure can be studied. Examples of complex surface structure include: simple thin films (in which case, for example, the parameter(s) of interest may be the film thickness, the refractive index of the film, the refractive index of the substrate, or some combination thereof); multilayer thin films; sharp edges and surface features that diffract or otherwise generate complex interference effects; unresolved surface roughness; unresolved surface features, for example, a sub-wavelength width groove on an otherwise smooth surface; dissimilar materials (for example, the surface may include a combination of thin film and a solid metal, in which case the library may include both surface structure types and automatically identify the film or the solid metal by a match to the corresponding frequency-domain spectra); surface structure that give rise to optical activity such as fluorescence; spectroscopic properties of the surface, such as color and wavelength-dependent reflectivity; polarization-dependent properties of the surface; and deflections, vibrations or motions of the surface or deformable surface features that result in perturbations of the interference signal.

The methods and techniques described herein can be used for in-process metrology measurements of semiconductor chips. For example, scanning interferometry measurements can be used for non-contact surface topography measurements semiconductor wafers during chemical mechanical polishing (CMP) of a dielectric layer on the wafer. CMP is used to create a smooth surface for the dielectric layer, suitable for precision optical lithography. Based on the results of the interferometric topography methods, the process conditions for CMP (e.g., pad pressure, polishing slurry composition, etc.) can be adjusted to keep surface non-uniformities within acceptable limits.

As used herein, "light" is not limited to electromagnetic radiation in the visible spectral region, but rather refers generally to electromagnetic radiation in any of the ultraviolet, visible, near infrared, and infrared spectral regions.

Unless otherwise defined, all technical and scientific terms used herein have the same meaning as commonly understood by one of ordinary skill in the art to which this invention belongs. In case of conflict with any document incorporated by reference, the present disclosure controls.

Other features and advantages will be apparent from the following detailed description.

BRIEF DESCRIPTION OF THE DRAWINGS

Like reference numerals in different drawings refer to common elements.

DETAILED DESCRIPTION

Figure 1:
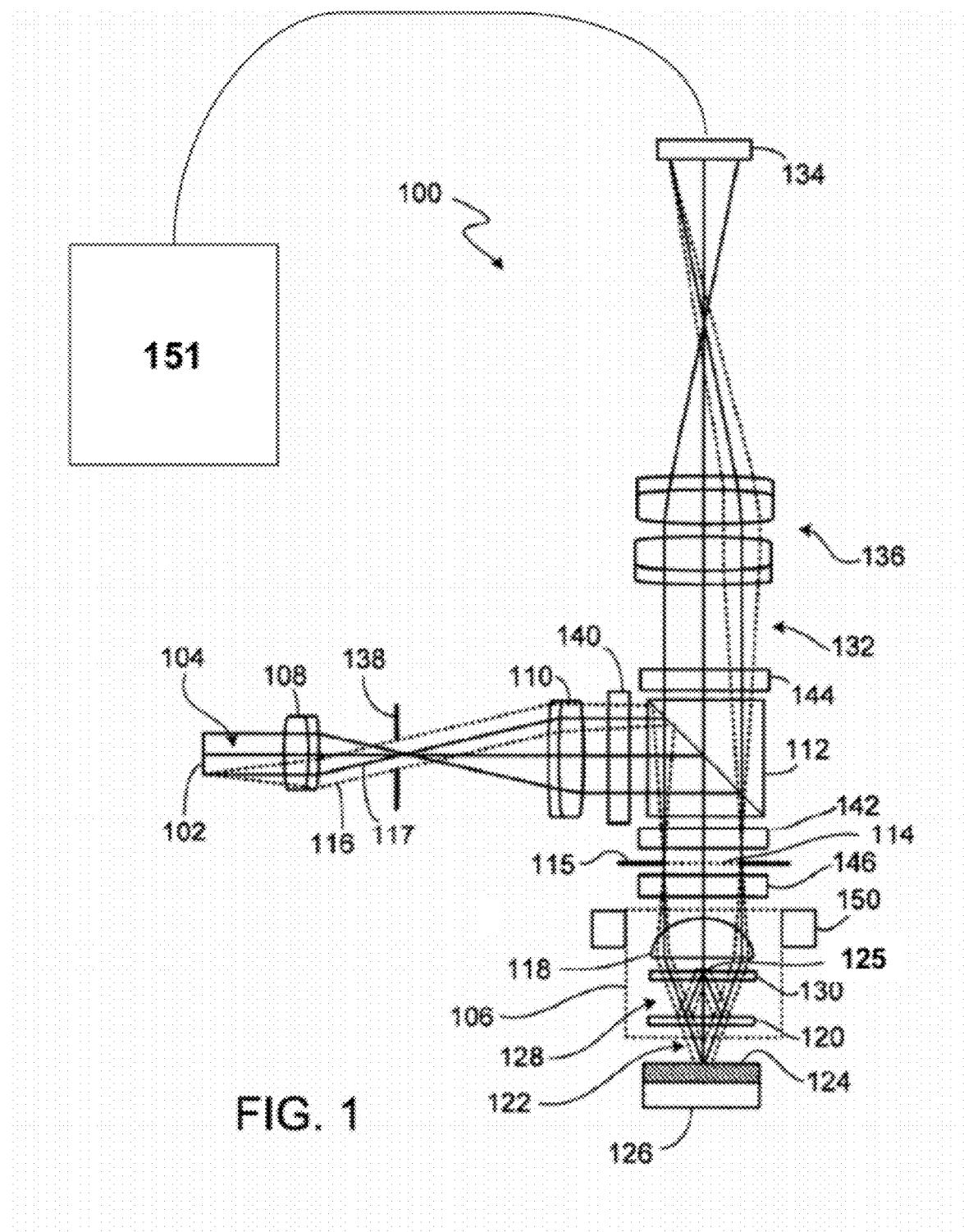
FIG. 1 is a schematic diagram of an embodiment of an interferometry system.

The complex reflectivity of a test object at multiple different wavelengths can be measured using an interferometry system. For example, FIG. 1 is a schematic diagram of an interferometry system 100, of the type described in U.S. Patent Publication No. 2006-0158659-A1 "INTERFEROMETER FOR DETERMINING CHARACTERISTICS OF AN OBJECT SURFACE" by Xavier Colonna de Lega et. al., U.S. Patent Publication No. 2006-0158658-A "INTERFEROMETER WITH MULTIPLE MODES OF OPERATION FOR DETERMINING CHARACTERISTICS OF AN OBJECT SURFACE", by Xavier Colonna de Lega et. al., and U.S. Patent Publication No. 2006-0158657"A INTERFEROMETER FOR DETERMINING CHARACTERISTICS OF AN OBJECT SURFACE, INCLUDING PROCESSING AND CALIBRATION" by Xavier Colonna de Lega et. al., each of which is incorporated herein by reference.

Interferometry system 100 includes a source 102 (e.g., a spatially extended source) that directs input light 104 to an interference objective 106 via relay optics 108 and 110 and beam splitter 112. The relay optics 108 and 110 image input light 104 from spatially extended source 102 to an aperture stop 115 and corresponding pupil plane 114 of the interference objective 106 (as shown by the dotted marginal rays 116 and solid chief rays 117).

In the embodiment of FIG. 1, interference objective 106 is of the Mirau-type, including an objective lens 118, beam splitter 120, and reference surface 125. Beam splitter 120 separates input light 104 into test light 122, which is directed to a test surface 124 of a test object 126, and reference light 128, which reflects from reference surface 125. Objective lens 118 focuses the test and reference light to the test and reference surfaces, respectively. The reference optic 130 supporting reference surface 125 is coated to be reflective only for the focused reference light, so that the majority of the input light passes through the reference optic before being split by beam splitter 120.

After reflecting from the test and reference surfaces, the test and reference light are recombined by beam splitter 120 to form combined light 132, which is transmitted by beam splitter 112 and relay lens 136 to form an optical interference pattern on an electronic detector 134 (for example, a multi-element CCD or CMOS detector). The intensity profile of the optical interference pattern across the detector is measured by different elements of the detector and stored in an electronic processor (not shown) for analysis. Unlike a conventional profiling interferometer in which the test surface is imaged onto the detector, in the present embodiment, relay lens 136 (e.g., a Bertrand lens) images different points on the pupil plane 114 to corresponding points on detector 134 (again as illustrating by dotted marginal rays 116 and solid chief rays 117).

Because each source point illuminating pupil plane 114 creates a plane wave front for test light 122 illuminating test surface 124, the radial location of the source point in pupil plane 114 defines the angle of incidence of this illumination bundle with respect to the object normal. Thus, all source points located at a given distance from the optical axis correspond to a fixed angle of incidence, by which objective lens 118 focuses test light 122 to test surface 124. A field stop 138 positioned between relay optic 108 and 110 defines the area of test surface 124 illuminated by test light 122. After reflection from the test and reference surfaces, combined light 132 forms a secondary image of the source at pupil plane 114 of the objective lens. Because the combined light on the pupil plane is then re-imaged by relay lens 136 onto detector 134, the different elements of the detector 134 correspond to the different illumination angles of test light 122 on test surface 124.

In some embodiments, polarization elements 140, 142, 144, and 146 are optionally included to define the polarization state of the test and reference light being directed to the respective test and reference surfaces, and that of the combined light being directed to the detector. Depending on the embodiment, each polarization element can be a polarizer (e.g., a linear polarizer), a retardation plate (e.g., a half or quarter wave plate), or a similar optic that affects the polarization state of an incident beam. Furthermore, in some embodiments, one or more of the polarization elements can be absent. In some embodiment these elements are adjustable, for instance mounted on a rotation mount, and even motorized under electronic control of the system. Electronically controlled liquid crystal cells can also be used to control polarization state of the various beam paths. Patterned liquid crystal cells can even provide pixelated control of polarization state at the pupil, such that each individual source point has a specific polarization state of illumination. Moreover, depending on the embodiment, beam splitter 112 can be a polarizing beam splitter or a non-polarizing beam splitter. In general, because of the presence of polarization elements 140, 142 and/or 146, the state of polarization of test light 122 at test surface 124 can be a function of the azimuthal position of the light in pupil plane 114.

In the presently described embodiment, source 102 provides illumination over a broad band of wavelengths (e.g., an emission spectrum having a full-width, half-maximum of more than 50 nm, or preferably, even more than 100 nm). For example, source 102 can be a white light emitting diode (LED), a filament of a halogen bulb, an arc lamp such as a Xenon arc lamp or a so-called supercontinuum source that uses non-linear effects in optical materials to generate very broad source spectra (e.g., >200 nm). The broad band of wavelengths corresponds to a limited coherence length.

A translation stage 150 adjusts the relative optic path length between the test and reference light to produce an optical interference signal at each of the detector elements. For example, in the embodiment of the FIG. 1, translation stage 150 is a piezoelectric transducer coupled to interference objective 106 to adjust the distance between the test surface and the interference objective, and thereby vary the relative optical path length between the test and reference light at the detector. The scanning interferometry signals are recorded at detector 134 and processed by a computer 151 that is in communication with the detector.

The scanning interferometry signal measured at each detector element is analyzed by the computer, which is electronically coupled to both detector 134 and translation stage 150. During analysis, computer 151 (or other electronic processor) determines the wavelength-dependent, complex reflectivity of the test surface from the scanning interferometry signal. For example, the scanning interferometry signal at each detector element can be Fourier transformed to give the magnitude and phase of the signal with respect to wavelength. This magnitude and phase can then be related to conventional ellipsometry parameters.

Synthetic Interference Signals

Analysis of the scanning interference signals generated using system 100 can be simplified by generating a synthetic interference signal from two or more of the scanning interference signals. As will be apparent from the description below, use of a synthetic interference signal can simplify the process of modeling scattering from the test object by removing some of its degrees of freedom. The general benefits can include improved computation throughput, reduced risk of model parameter cross-correlations and improved robustness, which may enable a further reduction in the amount of data that needs to be modeled to perform a meaningful measurement.

Generally, a synthetic interference signal is formed by combining two or more scanning interference signals in a way such that a contribution to the two or more scanning interference signals from a structure of the test object is suppressed or enhanced in the synthetic interference signal relative to the two or more scanning interference signals. Measured interference signals can be combined to form a synthetic interference signal in a variety of different ways. For example, the value of a measured interference signal at different scan positions (i.e., OPDs) can be combined with the value of one or more other simultaneously-acquired measured interference signals at the corresponding scan positions to provide the synthetic interference signal. Combining the values can include summing the values, e.g., as part of averaging the values. The sum (and correspondingly, the average) of the values can be a weighted sum (e.g., a weighted average). The values can be weighted according to a weighting function (see discussion below).

As an example, consider an application where the goal is to characterize the refractive index of a transparent layer on the test object (e.g., a layer of a dielectric material on a semiconductor wafer). For methods such as conventional ellipsometry or reflectometry the measured data depend not only on the material properties but also on the possibly unknown layer thickness. Thus, both attributes of the layer need to be present in any model used for data analysis, even though only the refractive index is of interest. This can complicate the model and create the potential for larger uncertainties in the measurement in cases where cross-correlations occur between the degrees of freedom of the numerical model.

Ideally, one would want to build a data analysis model that does not depend on the unknown film thickness. However, this typically requires measured data of a different nature. U.S. Pat. No. 7,446,882, entitled "Interferometer for Determining Characteristics of an Object Surface," issued on Nov. 4, 2008, for example, offers a scanning interferometric solution for the case where the layer is so thick that the interference signals associated with each material interface are clearly separated during the OPD scan. In this case one can isolate the signal from the interface of interest and process the scanning interferometry information as if the sample was a layer of infinite thickness. This approach takes advantage of the interferometric nature of the data collected in the scanning interferometry and of the limited coherence length of the light source in particular.

The method of U.S. Pat. No. 7,446,882 does not apply for films nominally thinner than the temporal coherence length of the source. However, combining certain of the scanning interference signals allows one to leverage the spatial and temporal coherence of the light source in order to generate a synthetic interference signal that is, to first order, identical to the scanning interference signal one would get from an infinitely thick slab of material. In other words, the contribution to the scanning interference signals from the buried interface between the transparent layer of interest and the underlying layer can be eliminated from the synthetic interference signal.

In the following discussion we use the example of a 1-μm thick nitride film on silicon to illustrate use of a synthetic interference signal. For this example, consider a source spectrum that spans the spectral domain 400-800 nm and the microscope objective captures light over a 12°-58° range of polar scattering angles (corresponding to a 0.85 NA Mirau objective).

Figure 2:
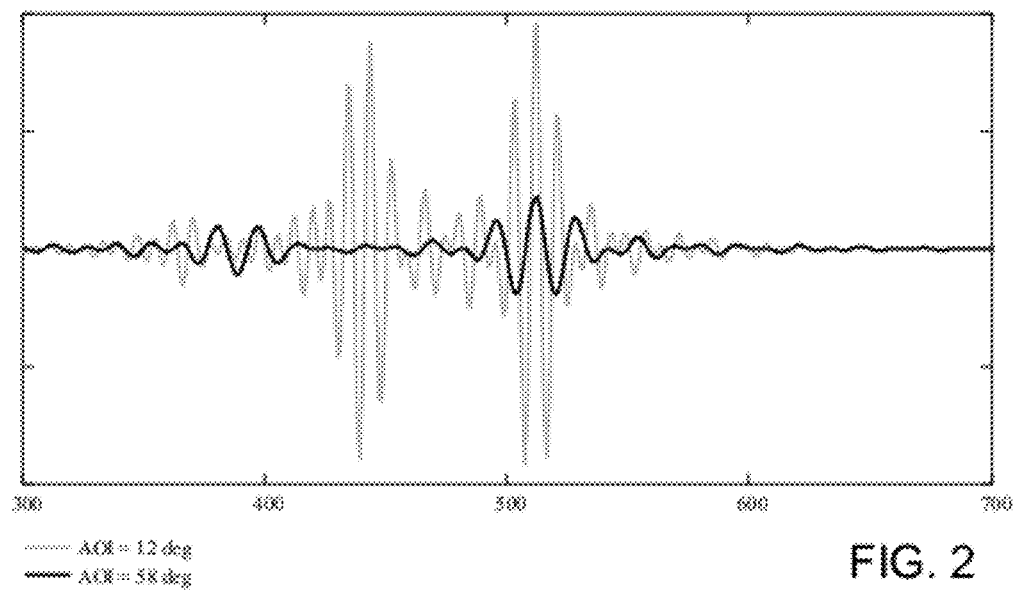
FIG. 2 is a plot showing simulated interference signals at two different angles of incidence when measuring a 1-μm thick nitride film with S-polarized light. The dark trace corresponds to an angle of incidence of 58°. The light trace corresponds to an angle of incidence of 12°.
Figure 3:
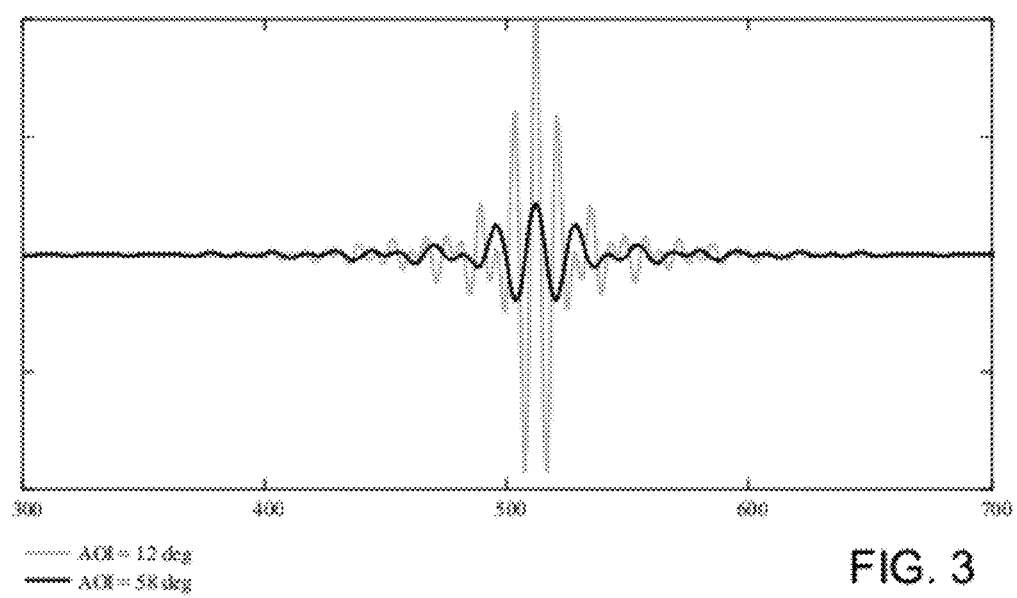
FIG. 3 is a plot showing simulated interference signals at angles of incidence 58° (dark trace) and 12° (light trace) for an infinitely thick nitride film with S-polarized light.

FIGS. 2 and 3 show theoretical interference signals for two angles of incidence for the 1-μm thick nitride film on silicon and an infinitely thick nitride film, respectively. The dark line corresponds to an angle of incidence of 58°, while the lighter-colored line corresponds to an angle of incidence of 12°. The presence of a film is clearly visible in FIG. 2 where one observes two distinct groups of oscillations in each signal. Specifically, one observes the signals corresponding to the air/nitride interface centered about the same scan position (near position 510 on the x-axis of the plot) in both FIGS. 2 and 3, whereas the signals corresponding to the buried nitride/silicon interface are spread over different scan locations for these two angles of incidence (440 and 380). Use of a synthetic interference signal allows one to use this variation in signal location to strongly attenuate it or even eliminate it.

While a variety approaches may be used to generate a synthetic interference signal, for the present embodiment, one can compute a weighted sum of signal values corresponding to multiple different polar scattering angles along a constant azimuth. This corresponds to selecting interference signals along a common radius as measured from the optical axis in the pupil of the interferometry system. This yields a synthetic interference signal that, to first order, no longer carries information about the finite thickness of the layer.

More generally, depending on the feature of the test object whose contribution to the synthetic interference signal is to be reduced or enhanced, the scanning interference signals selected for combining to form the synthetic interference signal can vary. As discussed in the present example, in some embodiments, the signals can correspond to different polar scattering angles of the test light but along a common azimuthal scattering angle. In certain embodiments, scanning interference signals having a constant polar scattering angle, but different azimuths, can be selected. In such a case the variation of the polarization state of illumination light as a function of azimuth induces variations of the measured signal. Similarly, the optical response of patterned structures depends on the azimuth of the illuminating light, even if the illumination light itself has a constant state of polarization. These variations are again used to eliminate some unwanted signal component. In certain embodiments a set of azimuthal and polar locations are used to select interference signals to be combined. In this case both signal variations with azimuth and angle of incidence contribute to the reduction in unwanted signal features. A selection of pupil location can be for example over a set of radial positions repeated over a set of azimuthal positions or over a square distribution of locations in pupil space.

In general, ideal weights for the weighting function can be determined in a number of ways. For example, one option is to optimize the weights by minimizing the strength of the synthetic interference signal in a given region of the scan (for instance in the region where the film signature shows up—the signal modulation below scan positions of 500 in FIG. 2, for example). Another option includes optimizing the weights by minimizing the difference between the synthetic interference signal and another synthetic interference signal obtained by applying the same weights to data for an infinitely thick layer. Note that the signals used for computing the weights can be determined empirically (e.g., based on the interference signals measured for the test object or previously acquired interference signals) or the result of modeling. For example, weights can be determined based on interference signals determined by using models of structures under test, e.g., by generating a series of model signals and generating an optical synthetic interference signals using the weights as optimization parameters.

In some embodiments, it can be beneficial to force the weighting function to be continuous and smooth. This is accomplished, for example, by the use of a spline function that defines the distribution of weights as a function of angle of incidence. In this case the spline knots can be optimized using an iterative solver (for example Levenberg-Marquardt).

Figure 4:
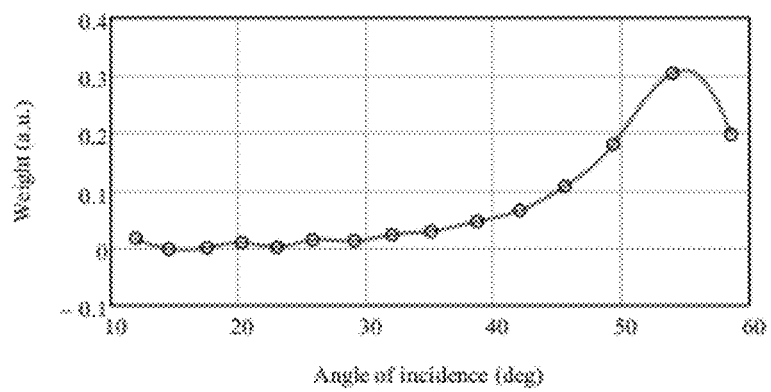
FIG. 4 is a plot showing a weighting function for generating a synthetic interference signal for a 1-μm thick nitride film.

Referring to FIG. 4, the exemplary weighting function that can be used for the data shown in FIG. 2 is shown. This weighting function is continuous and smooth, increasing from relative weights close to zero for low angles of incidence (e.g., less than) 30° and increasing to a maximum weight (0.3)

at an angle of incidence of approximately 55° before decreasing to a relative weight of 0.2 at 58°, the maximum angle of incidence for the model system.

Figure 5:
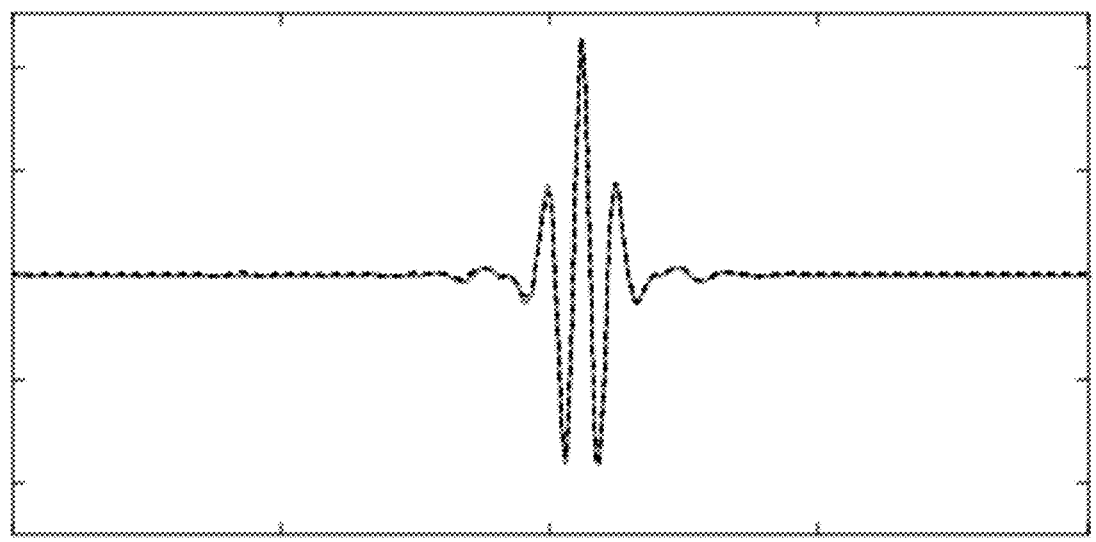
FIG. 5 is a plot comparing synthetic interference signals computed for an infinitely thick nitride film and a 1-μm thick nitride film. The synthetic interference signals are weighted sums of scanning interference signals spanning angles of incidence from 12°-58°, weighting using the weighting function shown in FIG. 4.

FIG. 5 shows the synthetic interference signals computed for the 1-μm thick nitride film and for an infinitely thick nitride layer. The synthetic signals are weighted sums of interference signals shown in FIGS. 2 and 3 spanning a 12°-58° range of angles of incidence. The synthetic interference signal for the 1 micron thick nitride film is identical to the synthetic interference signal for the infinitely thick sample, with the signal modulations at OPDs corresponding to the buried interface in the 1 micron thick film being eliminated.

Figure 6:
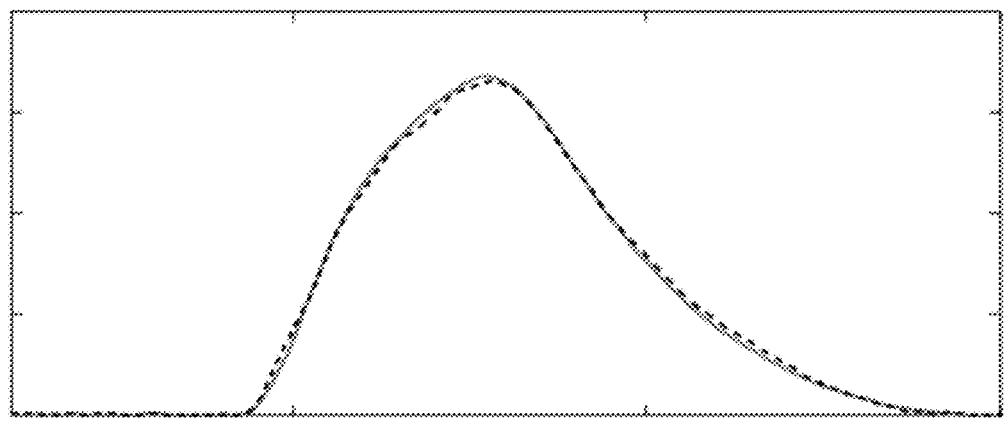
FIG. 6 is a plot comparing the spectral magnitude of the synthetic interference signals shown in FIG. 5.

FIG. 6 shows the spectral magnitudes of the two synthetic interference signals shown in FIG. 5. The root mean square difference ("RMS") between the two spectra is smaller than 0.8% of the maximum.

Figure 7:
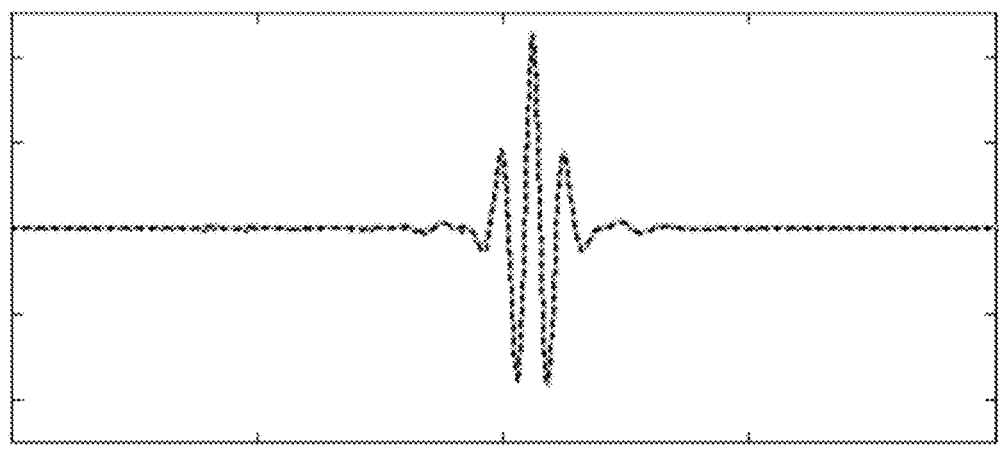
FIG. 7 is a plot comparing synthetic interference signals computed for nitride films with thicknesses ranging from 980 nm to 1040 nm.

FIG. 7 compares four synthetic interference signals corresponding to nitride film thicknesses ranging from 980 nm to 1040 nm. Each signal is generated using the same weighting function. This illustrates that the weights optimized for one particular thickness remain effective over a range of actual sample thicknesses, which is desired for the method to be effective in the presence of thickness variations from sample to sample.

In general, synthetic interference signals can be analyzed to provide information about the test object in a variety of ways. In some embodiments, synthetic interference signals can be analyzed by matching to signal libraries or by regression of the parameters of a model of the test object structure. In the example presented above (nitride film on silicon), the goal is to measure the optical properties of the film. One benefit is that the model used to generate library entries (or for the regression) is now significantly simpler since it ignores the presence of a substrate or the finite thickness of the layer. Note that when modeling is used, knowledge of the nominal film thickness and optical properties of the film and substrate are still needed. Such knowledge is not required when experimental data are available for both a sample with the nominal film thickness and a sample with a film sufficiently thick to be modeled as infinite.

In some embodiments, data analysis is confined to a subset of frequency components of the synthetic interference signal. Since the Fourier transform used to extract frequency components and the weighted average computation are linear mathematical processes one does not need to model all the spectral components present in the measured interference signal. Instead, if a single spatial frequency K is used for a given application, the data analysis can be performed by running the model at a single wavelength for each signal used in the weighted sum. This wavelength is selected such that the following relation is satisfied:

$$\frac{2\pi}{\lambda}\cos\alpha = K \quad (1)$$

where α is the angle of incidence for a given signal.

Figure 8:
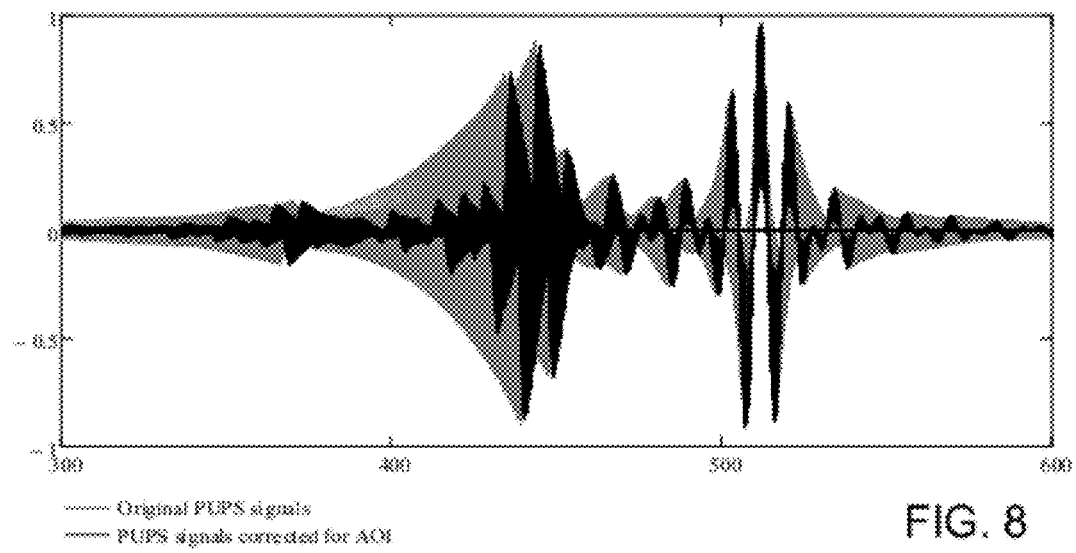
FIG. 8 is a plot showing scanning interference signals collected for various angles of incidence. The lighter-colored traces represent the original signals, while the black traces represent signals resampled at a common OPD scan rate.

In certain embodiments, it is possible to limit the analysis to specific spectral components of the light source. This can be performed, for example, by pre-processing the measured interference signals before computing the synthetic interference signal. Each signal can be Fourier transformed and the resulting spectrum used to compute a resampled signal using for example a Discrete Fourier Transform. The sampling step of the resampled signal matches the OPD step of a measured interference signal recorded at normal incidence. This amounts to "compressing" the x-axis (OPD axis) of the measured interference signals by an amount proportional to the cosine of the angle of incidence. Because the OPD scan rate is now the same for all signals a given frequency component of the final synthetic signal corresponds to a single spectral component of the light source. As an illustration, FIG. 8 displays original measured and resampled interference signals for the 1-μm thick nitride film.

While the foregoing example involves generating a single synthetic interference signal from multiple measured interference signals, other implementations are also possible. For example, in some embodiments, multiple synthetic interference signals can be generated from a single interferometry measurement. For example, one can use measured interference data collected for different azimuthal scattering angles, which correspond to different illumination conditions (e.g., polarization or sample orientation) and provide different interaction regimes with the sample. In some embodiments, where element 146 is a linear polarizer, data collected at azimuthal positions 0° and 180° with respect to the polarizer axis correspond to S polarization state for the illumination light. Similarly, light collected along radii at 90° and 270° correspond to P polarization for the illumination light. Most patterned layer structures will exhibit differences in optical response as a function of polarization. It follows that synthetic signals generated for S and P polarization will in general provide independent information about the sample, thus increasing the information content of a measurement.

Figure 9A:
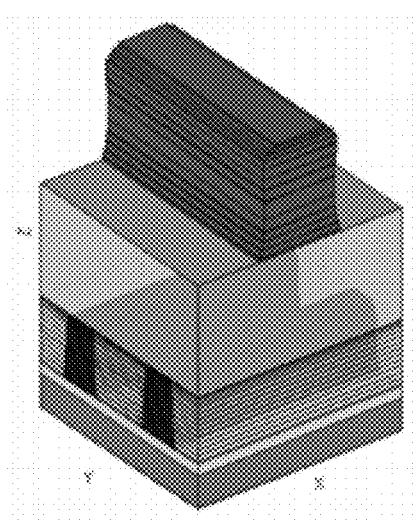
FIG. 9A is a perspective view of an integrated circuit structure showing one period of a repeating feature of interest located on top of unpatterned and patterned buried layers. The feature of interest is a set of parallel lines.
Figure 9B:
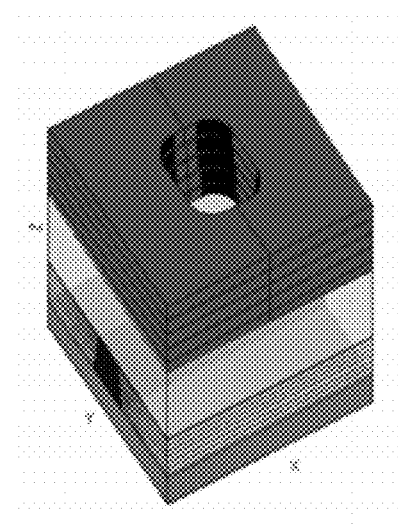
FIG. 9B is a plot showing perspective view of an integrated circuit structure showing one period of a repeating feature of interest located on top of unpatterned and patterned buried layers. The feature of interest is a regularly distributed pattern of holes.

The method can be particularly beneficial in the context of the characterization of semiconductor pattern structures. For example, linear gratings printed by photolithography into a photoresist layer are frequently used for process control in the semiconductor industry. In many applications the photoresist layer is the topmost layer of a stack that includes other patterned structures. FIGS. 9A and 9B show two such example structures. These examples feature semiconductor structures showing one period of a repeating feature of interest located on top of unpatterned and patterned buried layers. The feature of interest is a set of parallel lines (FIG. 9A) or a regularly distributed pattern of holes (FIG. 9B). A critical step of the manufacturing process consists in characterizing the dimensions of the photoresist structures before further processing. If the measured dimensions fall within specifications the wafer is sent for the next process step, typically an etch operation using the patterned photoresist layer as a mask. Conversely, if some attribute of the photoresist structure (for example its line width, sidewall angle, rounding, height, etc) is found to be outside of the process window the photoresist layer is removed and a new layer is deposited, patterned and developed. Similar metrology steps are required after transfer of the resist pattern to the underlying material layer by etching. Dummy buried periodic structures as shown in FIGS. 9A and 9B are typically used to achieve a design-rule-compliant pattern density for layers that are subjected to a Chemical Mechanical Polishing process step.

The complexity of the computations required to solve Maxwell's equations within such structures increases exponentially with the presence of buried patterns. Further complexity is introduced where the resulting model has to span three spatial dimensions, as would be the case for the structures of FIGS. 9A and 9B. Using the techniques described above one can create a synthetic interference signal devoid of the signature of such buried structures, which in turn enables the usage of a greatly simplified two-dimensional model with a single scattering topmost layer for a structure as shown in FIG. 9A. Three-dimensional modeling is generally still required for a three-dimensional structure such as the one shown in FIG. 9B. However, the computation is significantly simplified since the buried patterned grating can be omitted from the model.

In practice, the ability to fully suppress unwanted signal components depends strongly on the application. There may be cases where no weighting function can be found that fully eliminates the signature of buried layers from the synthetic signal. However, this signature can still be significantly reduced to the point where the model parameters that describe the buried layers can be approximated by their nominal or design value, thus ignoring possible process variations. These parameters then no longer represent degrees of freedom for the model regression or library search that determines the attributes of the layer of interest. This prevents cases of parameter cross-correlation and speeds up the regression or library search process.

In some embodiments, synthetic interference signals are generated after a pre-processing step that allows enhancing (e.g., maximizing) the signal information content of a buried interface instead of the topmost material interface. This pre-processing step may require some a priori knowledge of the optical properties and thickness of the layers covering the interface of interest. It is then possible to compute the optical path corresponding to the propagation of light through these layers, under different angles of incidence. Eq.(2) shows the corresponding phase change for a single layer:

$$\varphi(\lambda, a) = \frac{4\pi}{\lambda} t_1 \sqrt{n_1(\lambda)^2 - \sin(a)^2} \quad (2)$$

where $n_1(\lambda)$ and $t_1$ are respectively the refractive index and thickness of the first layer.

In embodiments where material layers covering the interface of interest the overall phase term can be computed as the sum of the phase contribution from each layer.

Here, the pre-processing procedure entails:
1. Fourier transforming the measured interference signal at each angle of incidence of interest;
2. Applying the phase correction term from Eq.(2) to each spectral component (in practice the math is written in terms of wavenumber instead of wavelength since the Fourier transform provides samples that are equi-spaced in wavenumber space)
3. Inverse transforming the modified spectrum, yielding a new signal.

Figure 10:
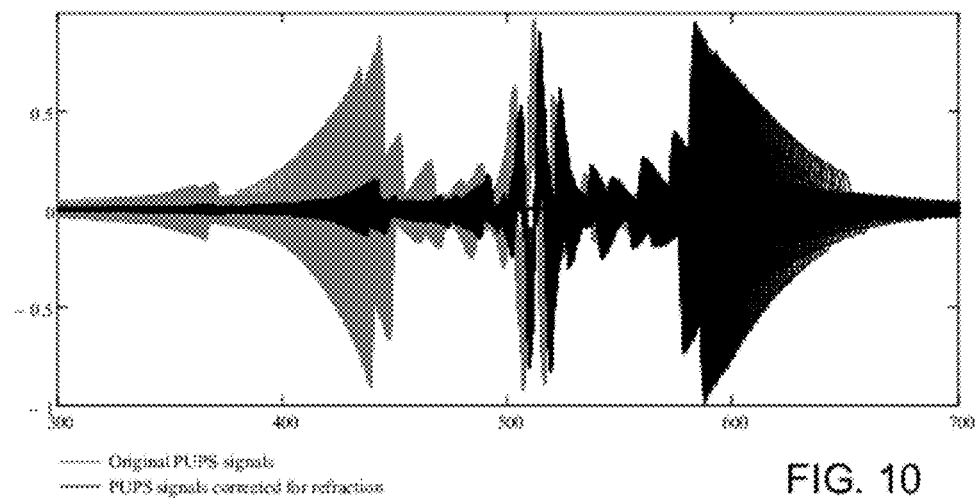
FIG. 10 is a plot showing scanning interference signals collected for various angles of incidence. The lighter-colored traces represent the original signals, while the black traces represent signals that have been corrected for the effect of refraction and propagation through the nitride layer in order to increase the signal from the buried interface between the nitride layer and the underlying substrate.

The resulting corrected signals become the new inputs for the weighted-sum computation of a synthetic interference signal. FIG. 10 shows the original measured interference signals (lighter colored) and the corrected signals (darker colored) when applying this procedure to the 1-μm thick nitride film data. An overall shift of the corrected signals is observed, of the order of the optical thickness of the transparent layer. As a result of the procedure the modulation of the interference signals corresponding to the buried interface are seen to overlap near the center of the plot (scan position 510), while the interference signals corresponding to the air/nitride interface are spread over a large scan range (from 580 to 650).

Figure 11:
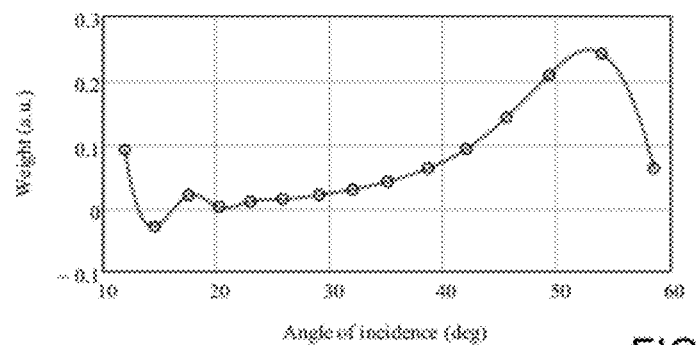
FIG. 11 is a plot showing a weighting function for generating a synthetic interference signal for a 1-μm thick nitride film when enhancing the signal component from the buried interface.

The procedure for determining the weighting factors is similar to the one described earlier. In this instance the goal is to wash out the signal from the air/nitride interface and the weights for the weighting function computed for this particular example are shown in FIG. 11.

Figure 12:
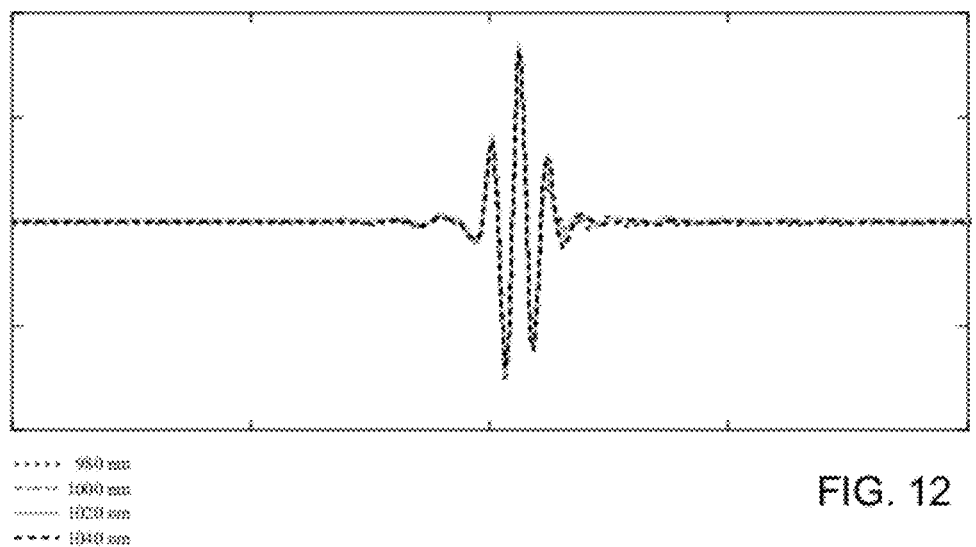
FIG. 12 is a plot comparing synthetic interference signals enhancing a buried interface computed for nitride films with thicknesses ranging from 980 nm to 1040 nm.

FIG. 12 shows the resulting synthetic signals for four different nitride film thicknesses. For this analysis the film thickness is assumed nominally known. The large signal components for the air/nitride interface (seen around location 600 in FIG. 10) are essentially eliminated while small differences remain between the synthetic signals localized at the buried interface. This demonstrates the benefit of the method in "focusing" the information content on the interface of interest. Further data analysis can be performed as discussed earlier for the top material interface. In this case however the finite transparent layer thickness should be included in the model.

While the foregoing description considers data acquired using interferometry system 100, implementations using other systems is also possible. Generally, the techniques disclosed herein can be applied to variations of interferometry system 100. For example, in some embodiments, interferometry system 100 can include polarizing beam splitter (i.e., beamsplitter 112 is a polarizing beam splitter) and no further polarizers or wave plates. For example, beamsplitter 112 can include two regions having mutually orthogonal pass axes. Incoming light enters pupil plane 114 in one polarization state and has to undergo a polarization change in order not to be blocked by the polarizing beam splitter upon reflection from the test object. The structures on the overlay target generally cause a polarization change, the extent of which is structure dependent. For symmetry reasons, the polarization state of x or y polarized beams is not changed by the gratings if the azimuth angle is equal to 0° or 180° and therefore beams having those polarization states are blocked by the analyzer and do not contribute to an interference signal.

In some embodiments, two polarizers having differing orientations are positioned at or near pupil plane 114, each one being positioned in only part of the optical path in the interference microscope.

In some embodiments, similar optical asymmetry can be introduced by the interferometry system hardware where polarizer and analyzer are parallel to one another, for instance to characterize critical dimensions of a test structure. For example, this can be accomplished by introducing a set of polarizing elements between the polarizing beam splitter cube and the microscope objective. That set of polarizing elements may be, e.g., a quarter wave plate followed by a polarizer oriented at 0° or 90°, a half wave plate followed by a polarizer oriented at 0° or 90° or a polarizer oriented at 45° followed by a polarizer oriented at 0° or 90° (angles with respect to x axis in FIG. 5). The insertion/removal of these two elements can be motorized to allow rapid switching from a cross-polarizer to a parallel-polarizer configuration. Such arrangements can enable a single instrument to perform both CD and overlay measurements, for example.

In some embodiments, a dissimilar polarizer-analyzer configuration is realized by using a non-polarizing beam splitter cube, placing a polarizer in the illumination leg in front of the beam splitter cube and an analyzer in the imaging leg after the beam splitter cube. Similar to the previous configuration, this configuration allows switching between a regular scanning interferometer setup (i.e., parallel polarizer and analyzer) and a dissimilar polarizer-analyzer configuration where the polarizer/analyzer orientation is controlled (e.g., by means of mechanical rotary stages or active polarization elements such as an electrically controlled LCD).

For an idealized Mirau objective, the polarization state of the reference beam would not change on its path through the objective. Consequently, in such a system, reference light is blocked by the polarizing beam splitter on the way to the camera preventing any interference signal. In practice, however, the reference light significantly changes its polarization state on its way through the objective (e.g., due to interaction with coated optics with optical power-beam splitter-reference mirror-beam splitter-coated optics with optical power). A portion of the reference light is therefore able to pass the polarizing beam splitter and is available for interference with the light coming from the overlay target. The polarization state of x or y polarized beams is not expected to change in the reference path if the azimuth angle of the polarization is equal to 0°, 90°, 180° or 270° and therefore those beams are blocked by the polarizing beam splitter. In some embodiments, homogeneity of the reference light across the pupil can be improved by including a polarization changing element in the reference path. For example, in some embodiments, a wave plate can be included in the reference path. Alternatively, or additionally, a structured reference mirror with grating lines oriented at 45° can be used.

While the interference microscope shown in FIG. 1 is a Mirau-type microscope, other types of microscope can also be used. For example, in some embodiments, a Linnik-type interference microscope can be used. In certain embodiments, a Linnik-type microscope can provide more flexibility for modulating polarization of the reference beam because the reference beam path is physically more accessible relative to a Mirau-type objective. A quarter-wave plate in the collimated space of the reference path, for example, can be provided to cause a rotation of the polarization in double-pass and therefore provide a completely illuminated pupil as seen by the camera. The use of a Linnik-type interference microscope can also allow adjusting the reference light intensity with respect to the test light intensity in order to maximize the fringe contrast. For example, a neutral density filter can be positioned in the path of the reference light to reduce its intensity as necessary.

Adjustment of the reference light intensity relative to the test light intensity can also be done with a polarized Mirau objective, e.g., in which the beam splitter is sandwiched between two quarter wave plates. In such configurations, the reference and test light have orthogonal polarization states. Placing an analyzer aligned with the reference light polarization (lighting the entire pupil) can cause the test light to experience a dissimilar polarizer/analyzer configuration.

While a particular interferometry system is shown in FIG. 1, in general, the methods can be implemented using with a wide variety of optical systems that provide reflectivity measurements. Variations of the described interferometric systems can be used. For example, while the light source described for interferometry system 100 is a broadband light source, in general, interferometry systems used for overlay measurements may use monochromatic or broadband light sources. Further, the light source can be a spatially extended light source, e.g., filling the pupil of the objective (e.g., Köhler illumination); but a single source point imaged onto the sample is also feasible and also provides data for an extended range of illumination angles (e.g., for the full pupil).

Furthermore, interferometry systems used for reflectivity measurements can, in embodiments, be used for other types of metrology as well. For example, interferometry system 100 can be used for surface profiling measurements in addition to reflectivity measurements. In some embodiments, interferometry systems can also be adapted for additional functionality by switching between various hardware configurations. For example, the system hardware can be switched between conventional SWLI imaging and PUPS imaging, allowing, e.g., surface profile measurements to be made alongside reflectivity measurements.

Figure 13:
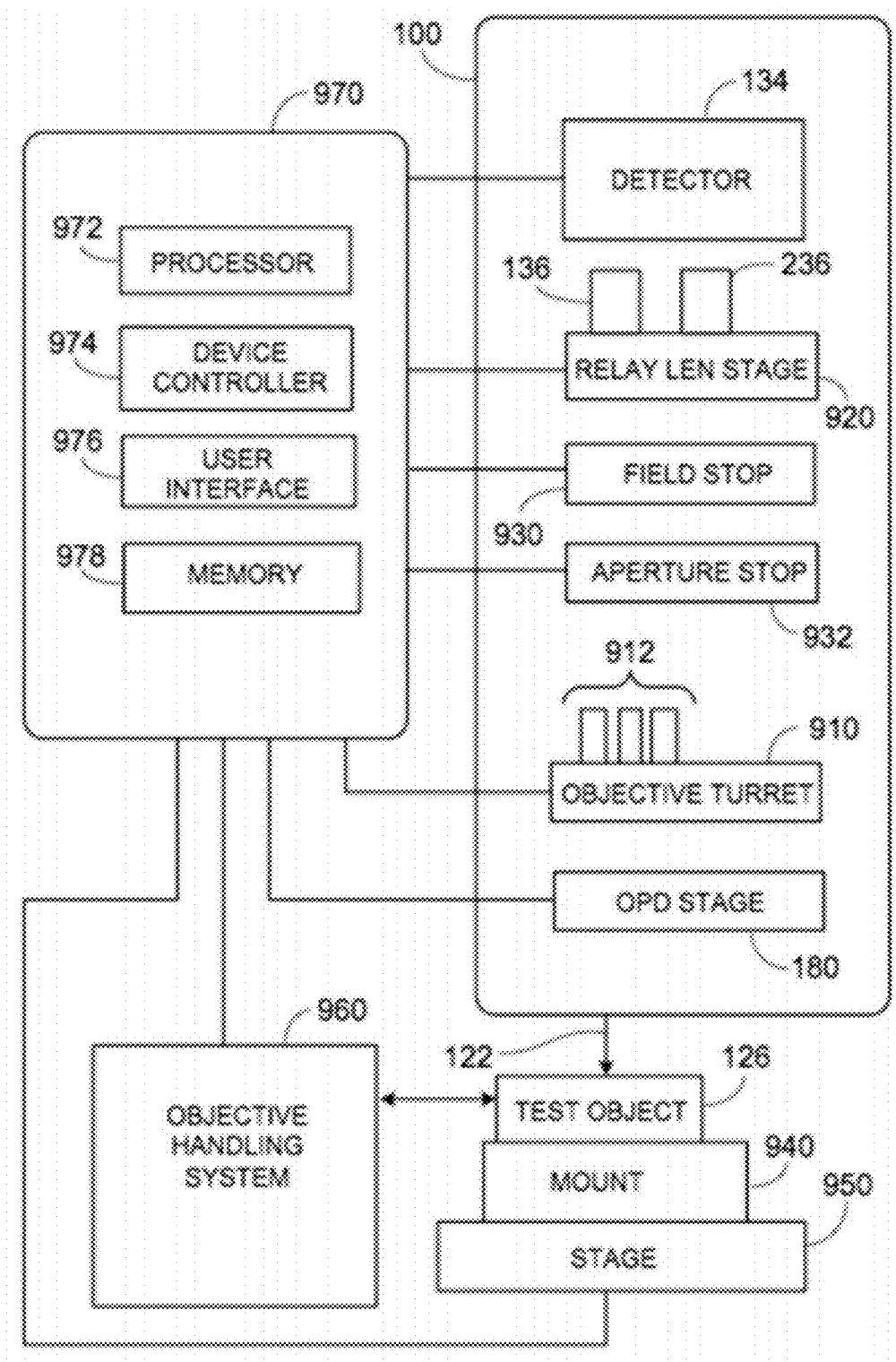
FIG. 13 is a schematic diagram of an embodiment of an interferometry system.

FIG. 13 shows a schematic diagram of how various components in interferometry system 100 can be automated under the control of electronic processor 970, which, in the presently described embodiment, can include an analytical processor 972 for carrying out mathematical analyses, device controllers 974 for controlling various components in the interferometry system, a user interface 976 (e.g., a keyboard and display), and a storage medium 978 for storing calibration information, data files, a sample models, and/or automated protocols.

First, the system can include a motorized turret 910 supporting multiple objectives 912 and configured to introduce a selected objective into the path of input light 104. One or more of the objectives can be interference objectives, with the different interference objectives providing different magnifications. Furthermore, in certain embodiments, one (or more) of the interference objectives can be especially configured for the ellipsometry mode (e.g., PUPS mode) of operation by having polarization element 146 (e.g., a linear polarizer) attached to it. The remaining interference objectives can be used in the profiling mode and, in certain embodiments, can omit polarization element 146 so as to increase light efficiency (such as for the embodiment described above in which beam splitter 112 is a polarizing beam splitter and polarization element is 142 is a quarter wave plate). Moreover, one or more of the objectives can be a non-interferometric objective (i.e., one without a reference leg), each with a different magnification, so that system 100 can also operate in a conventional microscope mode for collecting optical images of the test surface (in which case the relay lens is set to image of test surface to the detector). Turret 910 is under the control of electronic processor 970, which selects the desired objective according to user input or some automated protocol.

Next, the system includes a motorized stage 920 (e.g., a tube lens holder) for supporting relay lenses 136 and 236 and selectively positioning one of them in the path of combined light 132 for selecting between the first mode (e.g., an ellipsometry or reflectometry mode) in which the pupil plane 114 is imaged to the detector and the second mode (e.g., profiling/overlay or microscope mode) in which the test surface is imaged to the detector. Motorized stage 920 is under the control of electronic processor 970, which selects the desired relay lens according to user input or some automated protocol. In other embodiments, in which a translation stage is moved to adjust the position of the detector to switch between the first and second modes, the translation is under control of electronic processor. Furthermore, in those embodiments with two detection channels, each detector is coupled to the electronic processor 970 for analysis.

Furthermore, the system can include motorized apertures 930 and 932 under control of electronic processor 970 control the dimensions of field stop 138 and aperture stop 115, respectively. Again the motorized apertures are under the control of electronic processor 970, which selects the desired settings according to user input or some automated protocol.

Also, translation stage 150, which is used to vary the relative optical path length between the test and reference legs of the interferometer, is under the control of electronic processor 970. As described above, the translation stage can be coupled to adjust the position of the interference objective relative to a mount 940 for supporting test object 126. Alternatively, in further embodiments, the translation stage can adjust the position of the interferometry system as a whole relative to the mount, or the translation stage can be coupled to the mount, so it is the mount that moves to vary the optical path length difference.

Furthermore, a lateral translation stage 950, also under the control of electronic processor 970, can be coupled to the mount 940 supporting the test object to translate laterally the region of the test surface under optical inspection. In certain embodiments, translation stage 950 can also orient mount 940

(e.g., provide tip and tilt) so as to align the test surface normal to the optical axis of the interference objective.

Finally, an object handling station 960, also under control of electronic processor 970, can be coupled to mount 940 to provide automated introduction and removal of test samples into system 100 for measurement. For example, automated wafer handling systems known in the art can be used for this purpose. Furthermore, if necessary, system 100 and object handling system can be housed under vacuum or clean room conditions to minimize contamination of the test objects.

The resulting system provides great flexibility for providing various measurement modalities and procedures. For example, the system can first be configured in the microscope mode with one or more selected magnifications to obtain optical images of the test object for various lateral positions of the object. Such images can be analyzed by a user or by electronic processor 970 (using machine vision techniques) to identify certain regions (e.g., specific structures or features, landmarks, fiducial markers, defects, etc.) in the object. Based on such identification, selected regions of the sample can then be studied in the ellipsometry mode to determine sample properties (e.g., refractive index, underlying film thickness(es), material identification, etc.).

Accordingly, the electronic processor causes stage 920 to switch the relay lens to the one configured for the ellipsometry mode and further causes turret 910 to introduce a suitable interference objective into the path of the input light. To improve the accuracy of the ellipsometry measurement, the electronic processor can reduce the size of the field stop via motorized aperture 930 to isolate a small laterally homogenous region of the object. After the ellipsometry characterization is complete, electronic processor 970 can switch the instrument to the profiling mode, selecting an interference objective with a suitable magnification and adjusting the size of field stop accordingly. The profiling/overlay mode captures interference signals that allow reconstructing the topography of, for example, one or more interfaces that constitute the object. Notably, the knowledge of the optical characteristics of the various materials determined in the ellipsometry mode allows for correcting the calculated topography for thin film or dissimilar material effects that would otherwise distort the profile. See, for example, U.S. patent application Ser. No. 10/795,579 entitled "PROFILING COMPLEX SURFACE STRUCTURES USING SCANNING INTERFEROMETRY" and published as US Patent Publication No. US-2004-0189999-A1, which is incorporated by reference. If desired, the electronic processor can also adjust the aperture stop diameter via motorized aperture 932 to improve the measurement in any of the various modes.

When used in conjunction with automated object handling system 960, the measurement procedure can be repeated automatically for a series of samples. This could be useful for various process control schemes, such as for monitoring, testing, and/or optimizing one or more semiconductor processing steps.

For example, the system can be used in a semiconductor process for tool specific monitoring or for controlling the process flow itself. In the process monitoring application, single/multi-layer films are grown, deposited, polished, or etched away on unpatterned Si wafers (monitor wafers) by the corresponding process tool and subsequently the thickness and/or optical properties are measured using the interferometry system disclosed herein (for example, by using the ellipsometry mode, the profiling/overlay mode, or both). The average, as well as within wafer uniformity, of thickness (and/or optical properties) of these monitor wafers are used to determine whether the associated process tool is operating with targeted specification or should be retargeted, adjusted, or taken out of production use.

In the process control application, latter single/multi-layer films are grown, deposited, polished, or etched away on patterned Si, production wafers by the corresponding process tool and subsequently the thickness and/or optical properties are measured with the interferometry system disclosed herein (for example, by using the ellipsometry mode, the profiling mode, or both). Production measurements used for process control typical include a small measurement site and the ability to align the measurement tool to the sample region of interest. This site may consists of multi-layer film stack (that may itself be patterned) and thus requires complex mathematical modeling in order to extract the relevant physical parameters. Process control measurements determine the stability of the integrated process flow and determine whether the integrated processing should continue, be retargeted, redirected to other equipment, or shut down entirely.

Specifically, for example, the interferometry system disclosed herein can be used to monitor the following equipment: diffusion, rapid thermal anneal, chemical vapor deposition tools (both low pressure and high pressure), dielectric etch, chemical mechanical polishers, plasma deposition, plasma etch, lithography track, and lithography exposure tools. Additionally, the interferometry system disclosed herein can be used to control the following processes: trench and isolation, transistor formation, as well as interlayer dielectric formation (such as dual damascene).

In some embodiments, light source 102 in system 100 of FIG. 1 is replaced by a tunable monochromatic source under the control of the electronic processor. For example, the source can be a tunable laser diode or a broadband source incorporating a tunable spectral filter to produce a tunable spectral output (e.g., a monochromator, a spectral filter wheel, an acousto-optic tunable filter or a tunable liquid crystal filter.) Furthermore, the position of reference surface 125 (e.g., a reference mirror) is adjusted so that the optical path length difference between the test light and reference light when the test surface is in-focus with respect to the interference objective is non-zero. Detector 134 records the interference pattern produced by the combined light as the wavelength of the source is scanned. There is no mechanical motion of the object with respect to the interferometric objective in this case. Because of the adjustment in the position of the reference mirror and the resulting non-zero optical path length difference between the test and reference legs of the interferometer, the scanning of the source frequency produces an interference signal that is measured at each detector element. This interference signal is sometimes referred to as a "channel spectrum."

The embodiment shown in FIG. 1 uses an interference objective of the Mirau-type, in which the beam splitter in the interference objective directs the reference light back along the optical axis for the test light. In other embodiments, interferometry system 100 can instead use a different type of interference objective, such as a Michelson objective, in which the beam splitter directs the reference light away from the optical axis of the test light (e.g., the beam splitter can be oriented at 45 degrees to the input light so the test light and reference travel at right angles to one another). In such cases, the reference surface can be positioned outside of the path of the test light.

In some embodiments, the interference objective can be of the Linnik-type, in which case the beam splitter is positioned prior to the objective lens for the test surface (with respect to the input light) and directs the test and reference light along different paths. A separate objective lens is used to focus the reference light to the reference surface. In other words, the beam splitter separates the input light into the test and reference light, and separate objective lenses then focus the test and reference light to respective test and reference surfaces. Ideally the two objective lenses are matched to one another so that the test and reference light have similar aberrations and optical paths.

Additional interferometer configurations are also possible. For example, the system can be configured to collect test light that is transmitted through the test sample and then subsequently combined with reference light. For such embodiments, for example, the system can implement a Mach-Zehnder interferometer with dual microscope objectives on each leg.

The light source in the interferometer may be any of: an incandescent source, such as a halogen bulb or metal halide lamp, with or without spectral bandpass filters; a broadband laser diode; a light-emitting diode; a supercontinuum light source (as mentioned above); a combination of several light sources of the same or different types; an arc lamp; any source in the visible spectral region; any source in the IR spectral region, particularly for viewing rough surfaces & applying phase profiling; and any source in the UV spectral region, particularly for enhanced lateral resolution. For broadband applications, the source preferably has a net spectral bandwidth broader than 5% of the mean wavelength, or more preferably greater than 10%, 20%, 30%, or even 50% of the mean wavelength. For tunable, narrow-band applications, the tuning range is preferably broad (e.g., greater than 50 nm, greater than 100 nm, or greater than even 200 nm, for visible light) to provide reflectivity information over a wide range of wavelengths, whereas the spectral width at any particular setting is preferable narrow, to optimize resolution, for example, as small as 10 nm, 2 nm, or 1 nm. The source may also include one or more diffuser elements to increase the spatial extent of the input light being emitted from the source.

Furthermore, the various translations stages in the system, such as translation stage 150, may be: driven by any of a piezo-electric device, a stepper motor, and a voice coil; implemented opto-mechanically or opto-electronically rather than by pure translation (e.g., by using any of liquid crystals, electro-optic effects, strained fibers, and rotating waveplates) to introduce an optical path length variation; any of a driver with a flexure mount and any driver with a mechanical stage, e.g. roller bearings or air bearings.

The electronic detector can be any type of detector for measuring an optical interference pattern with spatial resolution, such as a multi-element CCD or CMOS detector.

The analysis steps described above can be implemented in computer programs using standard programming techniques. Such programs are designed to execute on programmable computers or specifically designed integrated circuits, each comprising an electronic processor, a data storage system (including memory and/or storage elements), at least one input device, and least one output device, such as a display or printer. The program code is applied to input data (e.g., scanning interference signals from the detector) to perform the functions described herein and generate output information (e.g., overlay error, refractive index information, thickness measurement(s), surface profile(s), etc.), which is applied to one or more output devices. Each such computer program can be implemented in a high-level procedural or object-oriented programming language, or an assembly or machine language. Furthermore, the language can be a compiled, interpreted or intermediate language. Each such computer program can be stored on a computer readable storage medium (e.g., CD ROM or magnetic diskette) that when read by a computer can cause the processor in the computer to perform the analysis and control functions described herein.

Interferometry metrology systems, such as those discussed previously, can be used in the production of integrated circuits to monitor and improve overlay between patterned layers. For example, the interferometry systems and methods can be used in combination with a lithography system and other processing equipment used to produce integrated circuits. In general, a lithography system, also referred to as an exposure system, typically includes an illumination system and a wafer positioning system. The illumination system includes a radiation source for providing radiation such as ultraviolet, visible, x-ray, electron, or ion radiation, and a reticle or mask for imparting the pattern to the radiation, thereby generating the spatially patterned radiation. In addition, for the case of reduction lithography, the illumination system can include a lens assembly for imaging the spatially patterned radiation onto the wafer. The imaged radiation exposes resist coated onto the wafer. The illumination system also includes a mask stage for supporting the mask and a positioning system for adjusting the position of the mask stage relative to the radiation directed through the mask. The wafer positioning system includes a wafer stage for supporting the wafer and a positioning system for adjusting the position of the wafer stage relative to the imaged radiation. Fabrication of integrated circuits can include multiple exposing steps. For a general reference on lithography, see, for example, J. R. Sheats and B. W. Smith, in *Microlithography: Science and Technology* (Marcel Dekker, Inc., New York, 1998), the contents of which is incorporated herein by reference.

Figure 14A:
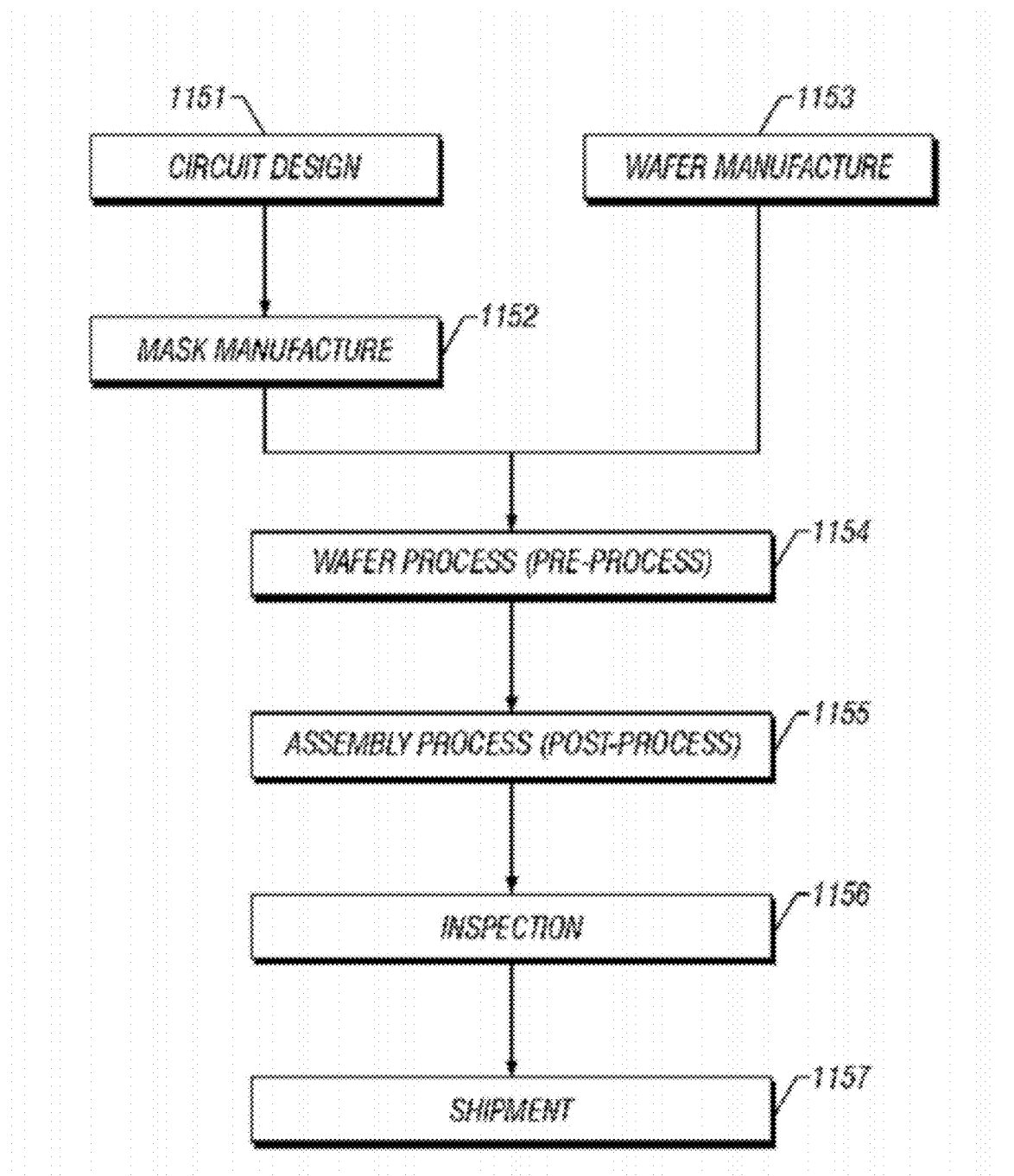
FIGS. 14A and 14B are flow charts that describe steps for producing integrated circuits.

As is well known in the art, lithography is a critical part of manufacturing methods for making semiconducting devices. For example, U.S. Pat. No. 5,483,343 outlines steps for such manufacturing methods. These steps are described below with reference to FIGS. 14A and 14B. FIG. 14A is a flow chart of the sequence of manufacturing a semiconductor device such as a semiconductor chip (e.g., IC or LSI), a liquid crystal panel or a CCD. Step 1151 is a design process for designing the circuit of a semiconductor device. Step 1152 is a process for manufacturing a mask on the basis of the circuit pattern design. Step 1153 is a process for manufacturing a wafer by using a material such as silicon.

Step 1154 is a wafer process which is called a pre-process wherein, by using the so prepared mask and wafer, circuits are formed on the wafer through lithography. To form circuits on the wafer, patterns from multiple masks are sequentially transferred to different layers on the wafer, building up the circuits. Effective circuit production requires accurate overlay between the sequentially formed layers. The interferometry methods and systems described herein can be especially useful to provide accurate overlay and thereby improve the effectiveness of the lithography used in the wafer process.

Step 1155 is an assembling step, which is called a post-process wherein the wafer processed by step 1154 is formed into semiconductor chips. This step includes assembling (dicing and bonding) and packaging (chip sealing). Step 1156 is an inspection step wherein operability check, durability check and so on of the semiconductor devices produced by step 1155 are carried out. With these processes, semiconductor devices are finished and they are shipped (step 1157).

Figure 14B:
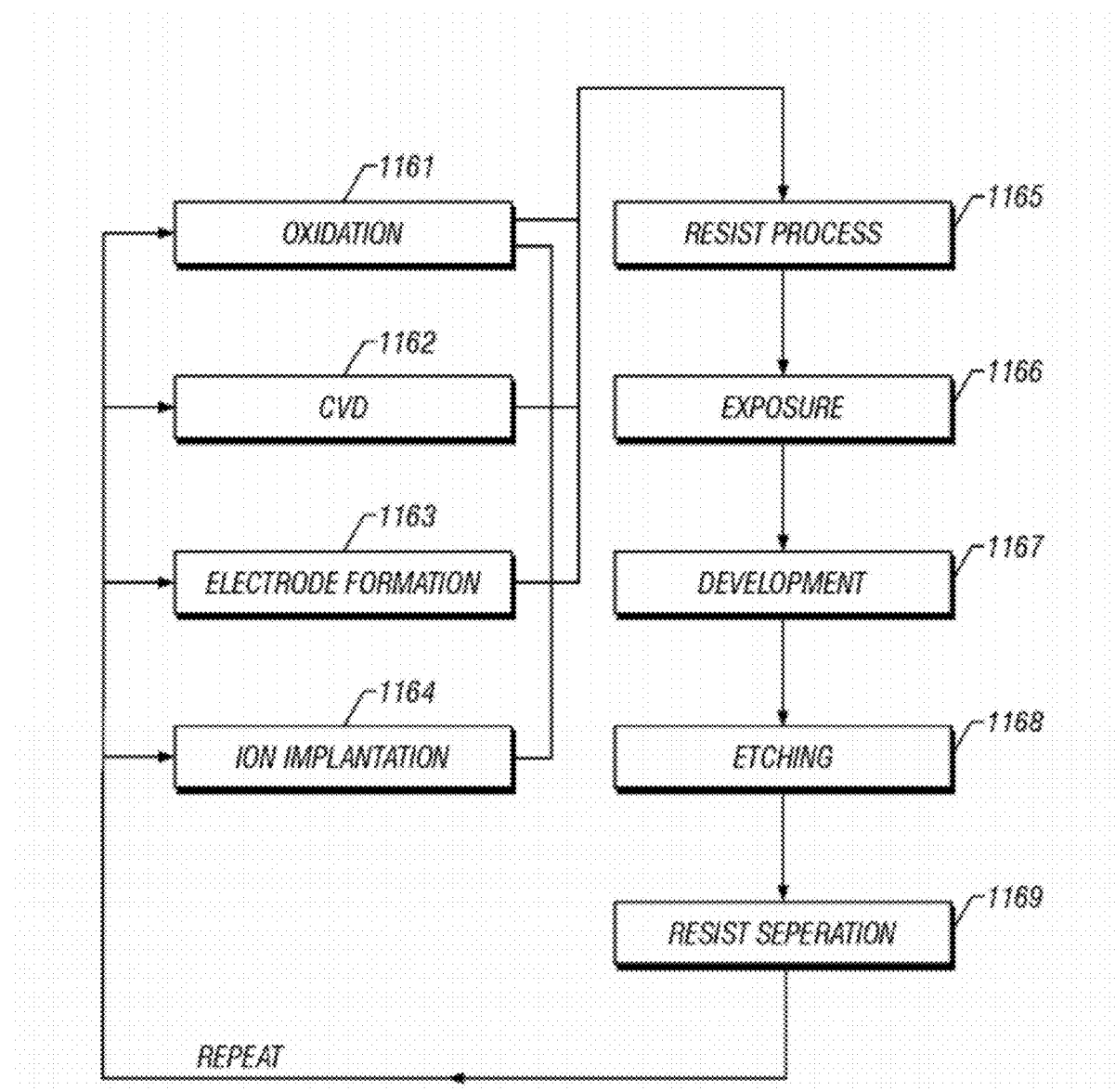

FIG. 14B is a flow chart showing details of the wafer process. Step 1161 is an oxidation process for oxidizing the surface of a wafer. Step 1162 is a CVD process for forming an insulating film on the wafer surface. Step 1163 is an electrode forming process for forming electrodes on the wafer by vapor deposition. Step 1164 is an ion implanting process for implanting ions to the wafer. Step 1165 is a resist process for applying a resist (photosensitive material) to the wafer. Step 1166 is an exposure process for printing, by exposure (i.e., lithography), the circuit pattern of the mask on the wafer through the exposure apparatus described above. Once again, as described above, the use of the interferometry systems and methods described herein can improve the accuracy and resolution of such lithography steps.

Step 1167 is a developing process for developing the exposed wafer. Step 1168 is an etching process for removing portions other than the developed resist image. Step 1169 is a resist separation process for separating the resist material remaining on the wafer after being subjected to the etching process. By repeating these processes, circuit patterns are formed and superimposed on the wafer.

As mentioned previously, the interferometry systems and methods disclosed herein can be used in the manufacture of flat panel displays such as, for example, liquid crystal displays (LCDs).

Figure 15:
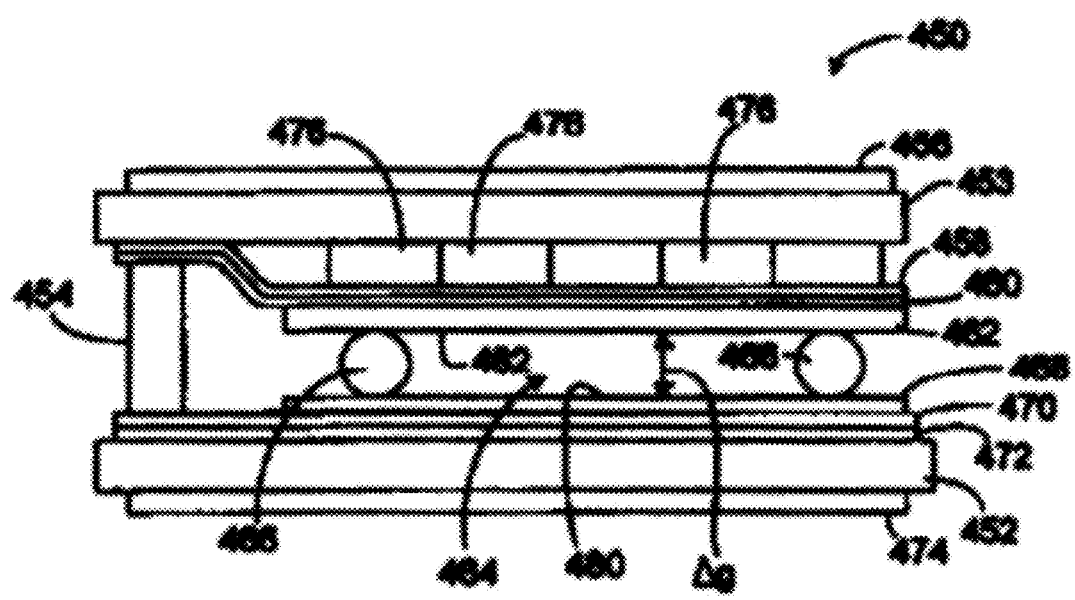
FIG. 15 is a schematic diagram of an embodiment of a LCD panel composed of several layers.

In general, a variety of different LCD configurations are used in many different applications, such as LCD televisions, desktop computer monitors, notebook computers, cell phones, automobile GPS navigation systems, automobile and aircraft entertainment systems to name a few. While the specific structure of a LCD can vary, many types of LCD utilize a similar panel structure. Referring to FIG. 15, for example, in some embodiments, a LCD panel 450 is composed of several layers including two glass plates 452,453 connected by seals 454. Glass plates 452 and 453 are separated by a gap 464, which is filled with a liquid crystal material. Polarizers 456 and 474 are applied to glass plates 453 and 452, respectively. One of the polarizers operates to polarize light from the display's light source (e.g., a backlight, not shown) and the other polarizer serves as an analyzer, transmitting only that component of the light polarized parallel to the polarizer's transmission axis.

An array of color filters 476 is formed on glass plate 453 and a patterned electrode layer 458 is formed on color filters 476 from a transparent conductor, commonly Indium Tin Oxide (ITO). A passivation layer 460, sometimes called hard coat layer, based on SiOx is coated over the electrode layer 458 to electrically insulate the surface. Polyimide 462 is disposed over the passivation layer 460 to align the liquid crystal fluid 464.

Panel 450 also includes a second electrode layer 472 formed on glass plate 452. Another hard coat layer 470 is formed on electrode layer 472 and another polyimide layer 468 is disposed on hard coat layer 470. In active matrix LCDs ("AM LCDs"), one of the electrode layers generally includes an array of thin film transistors (TFTs) (e.g., one or more for each sub-pixel) or other integrated circuit structures.

The liquid crystal material is birefringent and modifies the polarization direction of the light propagating through the material. The liquid crystal material also has a dielectric anisotropy and is therefore sensitive to electric fields applied across gap 464. Accordingly, the liquid crystal molecules change orientation when an electric field is applied, thereby varying the optical properties of the panel. By harnessing the birefringence and dielectric anisotropy of the liquid crystal material, one can control the amount of light transmitted by the panel.

The cell gap $\Delta g$, i.e., thickness of the liquid crystal layer 464, is determined by spacers 466, which keep the two glass plates 452, 453 at a fixed distance. In general, spacers can be in the form of preformed cylindrical or spherical particles having a diameter equal to the desired cell gap or can be formed on the substrate using patterning techniques (e.g., conventional photolithography techniques).

In general, LCD panel manufacturing involves multiple process steps in forming the various layers. For example, referring to FIG. 16, a process 499 includes forming the various layers on each glass plate in parallel, and then bonding the plates to form a cell. The cell is then filled with the liquid crystal material and sealed. After sealing, the polarizers are applied to the outer surface of each of the glass plates, providing the completed LCD panel.

Figure 16:
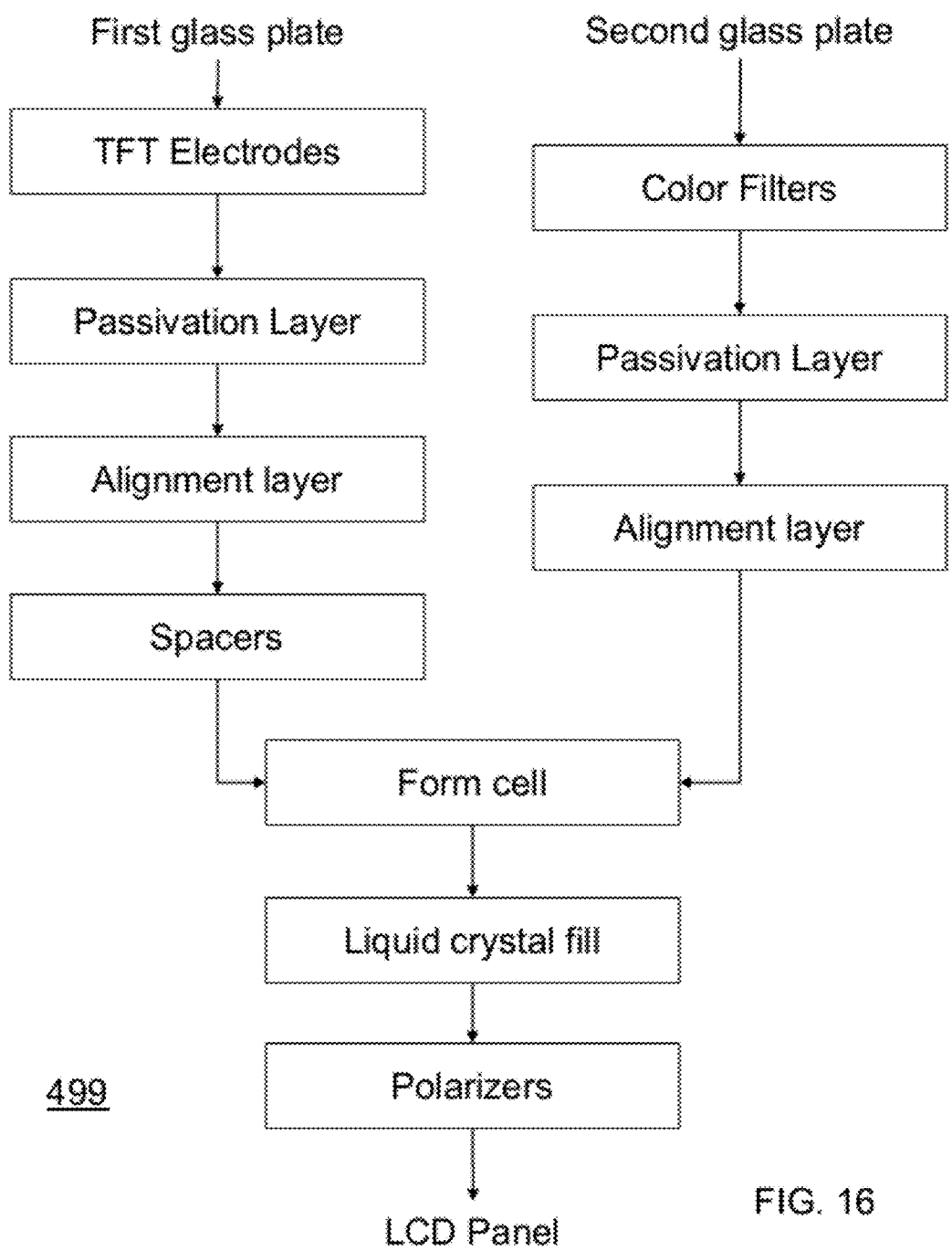
FIG. 16 is a flowchart showing various steps in LCD panel production.

In general, formation of each of the components illustrated in the flow chart in FIG. 16 can include multiple process steps. For example, in the present example, forming the TFT electrodes (commonly referred to as "pixel electrodes") on the first glass plate involves many different process steps. Similarly, forming the color filters on the second glass plate can involve numerous process steps. Typically, forming pixel electrodes include multiple process steps to form the TFTs, ITO electrodes, and various bus lines to the TFTs. In fact, forming the TFT electrode layer is, in essence, forming a large integrated circuit and involves many of the same deposition and photolithographic patterning processing steps used in conventional integrated circuit manufacturing. For example, various parts of the TFT electrode layer can be built by first depositing a layer of material (e.g., a semiconductor, conductor, or dielectric), forming a layer of photoresist over the layer of material, exposing the photoresist to patterned radiation. The photoresist layer is then developed, which results in a patterned layer of the photoresist. Next, portions of the layer of material lying beneath the patterned photoresist layer are removed in a etching process, thereby transferring the pattern in the photoresist to the layer of material. Finally, the residual photoresist is stripped from the substrate, leaving behind the patterned layer of material. These process steps can be repeated many times to lay down the different components of the TFT electrode layer.

In general, the interferometry techniques disclosed herein can be used to monitor overlay of different components of an LCD panel. For example, during panel production, the interferometry techniques can be used to determine overlay error between patterned resist layers and features beneath the photoresist layer. Where measured overlay error is outside a predetermined process window, the patterned photoresist can be stripped from the substrate and a new patterned photoresist layer formed.

Other embodiments are in the following claims.

What is claimed is:

1. A method for determining information about a test object, comprising:
   combining two or more scanning interference signals to form a synthetic interference signal, each of the two or more scanning interference signals resulting from detecting interference between test light and reference light as an optical path length difference between the test and reference light is scanned, the test and reference light being derived from a common source, and each of the two or more scanning interferometry signals corresponds to a different scattering angle or polarization state of the test light scattered from the test object;
   analyzing the synthetic interference signal to determine information about the test object; and
   outputting the information about the test object.

2. The method of claim 1, wherein a contribution to the two or more scanning interference signals from a structure of the test object is suppressed or enhanced in the synthetic interference signal relative to the two or more scanning interference signals.

3. The method of claim 2, wherein the structure is an interface between two different materials from which the test object is composed.

4. The method of claim 3, wherein a contribution from the interface to the two or more scanning interference signals is reduced in the synthetic interference signal.

5. The method of claim 2, wherein the structure is a first patterned structure of the test object.

6. The method of claim 5, wherein the information about the test object is information about a second patterned structure of the test object different from the first patterned structure.

7. The method of claim 6, wherein the first and second patterned structured are in different layers of the test object.

8. The method of claim 5, wherein the first patterned structure is a buried structure.

9. The method of claim 8, wherein a contribution from the first patterned structure to the two or more scanning interference signals is reduced in the synthetic interference signal.

10. The method of claim 5, wherein determining information about the test object comprises comparing the synthetic interference signal or information derived from the synthetic interference signal to model data, where the model data does not include a contribution from the first patterned structure.

11. The method of claim 5, wherein the first patterned structure comprises one or more holes in a layer of the test object.

12. The method of claim 5, wherein the first patterned structure comprises one or more lines of a grating of the test object.

13. The method of claim 5, wherein the first patterned structure comprises one or more mesas in the test object.

14. The method of claim 1, wherein the test object comprises a layer of a semiconductor material.

15. The method of claim 1, wherein the test object comprises a layer of a photoresist material.

16. The method of claim 15, wherein the layer of the photoresist materials is a patterned layer.

17. The method of claim 1, wherein combining the two or more scanning interference signals comprises combining values for the two or more scanning interference signals for each of multiple scan positions of the optical path length difference.

18. The method of claim 17, wherein combining the values comprises summing the values.

19. The method of claim 18, wherein summing the values comprises taking a weighted sum of the values.

20. The method of claim 19, wherein the values are weighted according to a predetermined weighting function.

21. The method of claim 19, wherein the weights for the weighted sum are determined based on a smoothly varying function.

22. The method of claim 21, wherein contributions to the synthetic interference signal from scanning interference signals corresponding to higher polar scattering angles are weighted more heavily that contributions corresponding to scanning interference signals from lower polar scattering angles.

23. The method of claim 18, wherein summing the values comprises averaging the values.

24. The method of claim 1, wherein combining the two or more scanning interference signals comprises weighting contributions from the two or more scanning interference signals to the synthetic interference signal so that a contribution to the synthetic interference signal from a structure of the test object is suppressed relative to a contribution from the structure to the two or more scanning interference signals.

25. The method of claim 1, wherein combining the two or more scanning interference signals comprises weighting contributions from the two or more scanning interference signals to the synthetic interference signal so that a contribution to the synthetic interference signal from a buried structure of the test object is enhanced relative to a contribution to the two or more scanning interference signals from the buried structure.

26. The method of claim 1, wherein the two or more scanning interference signals correspond to different polar scattering angles of the test light from the test object.

27. The method of claim 26, wherein the two or more scanning interference signals correspond to the same azimuthal scattering angle.

28. The method of claim 1, wherein determining information about the test object comprises comparing the synthetic interference signal or information derived from the synthetic interference signal to model data.

29. The method of claim 28, wherein comparing the synthetic interference signal to model data comprises matching the synthetic interference signal to a model signal in a library of model signals.

30. The method of claim 28, wherein comparing the synthetic interference signal to the model data comprises performing a regression of parameters of a model of the test object structure.

31. The method of claim 1, wherein the test object comprises a first layer of a material and the information about the test object is a refractive index of the material.

32. The method of claim 31, wherein a contribution from an interface between the first layer and an adjacent layer to the two or more scanning interference signals is reduced in the synthetic interference signal.

33. The method of claim 31, wherein determining information about the test object comprises comparing the synthetic interference signal or information derived from the synthetic interference signal to model data, where the model data is determined based on a model that does not depend on a thickness of the first layer.

34. The method of claim 1, wherein the synthetic interference signal comprises contributions from a plurality of frequency components and analysis of the synthetic interference signal is performed for only a subset of frequency components of the synthetic interference signal.

35. The method of claim 34, wherein analysis of the synthetic interference signal comprises determining a frequency transform of the synthetic interference signal.

36. The method of claim 35, wherein the frequency transform is a Fourier transform.

37. The method of claim 1, wherein determining information about the test object comprises comparing information derived from the synthetic interference signal to model data, where the model data is determined for a subset of wavelengths present in light used to generate the two or more scanning interference signals.

38. The method of claim 1, further comprises generating one or more additional synthetic interference signals from the one or more of the scanning interference signals.

39. The method of claim 38, wherein each of the synthetic interference signals corresponds to different illumination conditions of the test object.

40. The method of claim 39, wherein the different illumination conditions correspond to different polarization states of the test light.

41. A method for determining information about a test object, comprising:
    simultaneously acquiring two or more scanning interference signals, wherein each of the two or more scanning interference signals correspond to interference between test light and reference light as an optical path length difference between the test and reference light is scanned, wherein the test and reference light are derived from a common source, and wherein the test light scatters from the test object over a range of angles and each of the two or more scanning interferometry systems corresponds to a different scattering angle or polarization state of the test light;

combining values of the two or more scanning interference signals for each scan position of the optical path difference to form a combined signal in which a contribution to the combined signal from a feature of the test object is reduced relative to the contribution of the feature to the two or more scanning interferometry signals;

analyzing the combined signal to determine information about the test object; and outputting the information about the test object.

42. An apparatus comprising:

an interferometer configured to direct test light to a test surface over a range of illumination angles and subsequently combine it with reference light to form an interference pattern, the test and reference light being derived from a common source;

the common source;

a multi-element detector;

one or more optics configured to direct at least a portion of the combined light to the detector so that different elements of the detector correspond to different illumination angles of the test surface by the test light; and an electronic processing system coupled to the multi-element detector, which during operation receives two or more scanning interference signals from the multi-element detector, combines the two or more scanning interference signals to form a synthetic interference signal and analyzes the synthetic interference signal to determine information about the test object.

* * * * *

UNITED STATES PATENT AND TRADEMARK OFFICE
CERTIFICATE OF CORRECTION

| | |
|---|---|
| PATENT NO. | : 8,854,628 B2 |
| APPLICATION NO. | : 13/238732 |
| DATED | : October 7, 2014 |
| INVENTOR(S) | : Xavier M. Colonna de Lega, Peter J. de Groot and Jan Liesener |

It is certified that error appears in the above-identified patent and that said Letters Patent is hereby corrected as shown below:

IN THE CLAIMS:

Column 23

Line 56, in Claim 22, delete "that" and insert -- than --

Signed and Sealed this
Tenth Day of February, 2015

Michelle K. Lee
*Deputy Director of the United States Patent and Trademark Office*